US011793869B2

(12) United States Patent
Dhere et al.

(10) Patent No.: US 11,793,869 B2
(45) Date of Patent: Oct. 24, 2023

(54) METHODS FOR ENTEROVIRUS INACTIVATION, ADJUVANT ADSORPTION AND DOSE REDUCED VACCINE COMPOSITIONS OBTAINED THEREOF

(71) Applicant: SERUM INSTITUTE OF INDIA PVT LTD, Pune (IN)

(72) Inventors: Rajeev Mhalasakant Dhere, Pune (IN); Sambhaji Shankar Pisal, Pune (IN); Jagdish Kamalaji Zade, Pune (IN); Rajendra Narayan Sabale, Pune (IN); Hitesh Kumar Malviya, Pune (IN); Sunil Mahor, Pune (IN); Chetan Vilasrao Joshi, Pune (IN)

(73) Assignee: Serum Institute Of India Pvt Ltd., Maharashtra (IN)

( * ) Notice: Subject to any disclaimer, the term of this patent is extended or adjusted under 35 U.S.C. 154(b) by 0 days.

(21) Appl. No.: 16/597,964

(22) Filed: Oct. 10, 2019

(65) Prior Publication Data

US 2020/0085940 A1 Mar. 19, 2020

Related U.S. Application Data

(63) Continuation-in-part of application No. 15/517,225, filed as application No. PCT/IN2015/000376 on Oct. 6, 2015, now Pat. No. 10,485,862.

(30) Foreign Application Priority Data

Oct. 7, 2014 (IN) ......................... 3180/MUM/2014

(51) Int. Cl.

| | |
|---|---|
| *A61K 39/13* | (2006.01) |
| *A61K 39/04* | (2006.01) |
| *A61K 39/08* | (2006.01) |
| *A61K 39/102* | (2006.01) |
| *A61K 39/39* | (2006.01) |
| *C12N 7/00* | (2006.01) |
| *A61K 39/02* | (2006.01) |
| *A61K 39/05* | (2006.01) |
| *A61K 39/29* | (2006.01) |
| *A61K 39/00* | (2006.01) |

(52) U.S. Cl.
CPC .............. *A61K 39/13* (2013.01); *A61K 39/05* (2013.01); *A61K 39/08* (2013.01); *A61K 39/099* (2013.01); *A61K 39/102* (2013.01); *A61K 39/292* (2013.01); *A61K 39/39* (2013.01); *C12N 7/00* (2013.01); *A61K 2039/55505* (2013.01); *A61K 2039/70* (2013.01); *C12N 2730/10034* (2013.01); *C12N 2770/32634* (2013.01)

(58) Field of Classification Search
None
See application file for complete search history.

(56) References Cited

U.S. PATENT DOCUMENTS

| | | | | |
|---|---|---|---|---|
| 7,754,218 B2 * | 7/2010 | Contorni | ................. | A61P 31/04 424/184.1 |
| 2020/0034850 A1 * | 1/2020 | Weiss | ................. | G06Q 20/3674 |

FOREIGN PATENT DOCUMENTS

| | | | |
|---|---|---|---|
| WO | 2008028956 A1 | | 3/2008 |
| WO | WO 2011/074006 A2 | * | 6/2011 |

OTHER PUBLICATIONS

Jiang et al. Does a monovalent inactivated human rotavirus vaccine induce heterotypic immunity? Evidence from animal studies. Hum Vaccin Immunother. Aug. 1, 2013; 9(8): 1634-1637.*
Okada et al. Phase II and III Clinical Studies of Diphtheria-Tetanus-Acellular Pertussis Vaccine Containing Inactivated Polio Vaccine Derived from Sabin Strains (DTaP-sIPV). The Journal of Infectious Diseases 2013;208:275-83.*

* cited by examiner

*Primary Examiner* — Nianxiang Zou
(74) *Attorney, Agent, or Firm* — BakerHostetler; Tayan B. Patel

(57) ABSTRACT

The present invention is directed to improved methods of Enterovirus inactivation by formaldehyde in presence of tromethamine buffer resulting in maximum recovery of D-antigen. Subsequent adsorption of said sIPV on aluminium hydroxide provides significantly dose reduced sIPV compositions.

22 Claims, 5 Drawing Sheets

METHODS FOR ENTEROVIRUS INACTIVATION, ADJUVANT ADSORPTION AND DOSE REDUCED VACCINE COMPOSITIONS OBTAINED THEREOF

CROSS-REFERENCE TO RELATED APPLICATIONS

This application is a continuation-in-part of U.S. application Ser. No. 15/517,225, which is the U.S. National Phase of International Application No. PCT/IN2015/000376, filed Oct. 6, 2015 and published in English, which claims priority to Indian Provisional Application No. 3180/MUM/2014, filed Oct. 7, 2014. The disclosures of the above-identified applications are incorporated by reference in their entireties.

BACKGROUND

The prevalence of polio virus has largely been decreased by the use of Oral Polio Vaccine (OPV), based on live-attenuated Sabin polio strains. However, OPV has limitations for the post-eradication era. Therefore, development of Sabin-IPV plays an important role in the WHO polio eradication strategy. The use of attenuated Sabin instead of wild-type Salk polio strains will provide additional safety during vaccine production. Moreover, to prevent the emergence of circulating vaccine-derived polioviruses (cVDPVs), the use of OPV should be discontinued following polio eradication, and replaced by IPV. These cVDPVs are transmissible and can become neurovirulent (similar to wild polioviruses) resulting in vaccine associated paralytic poliomyelitis. Such strains can potentially re-seed the world with polioviruses and negate the eradication accomplishments.

IPV is delivered by intramuscular (IM) or deep subcutaneous (SC) injection. IPV is currently available either as a non-adjuvanted stand-alone formulation, or in various combinations, including DT-IPV (with diphtheria and tetanus toxoids) and hexavalentDTPHepB-Hib-IPV vaccines (additionally with pertussis, hepatitis B, and *Haemophilus influenzae* b. The currently acceptable standard dose of polio vaccines contains D antigens as 40 Units of inactivated poliovirus type 1 (Mahoney), 8 units of inactivated poliovirus type 2 (MEF-I) and 32 units of inactivated poliovirus type 3 (Saukett) (e.g. Infanrix-IPV™). Existing preparations of stand-alone IPV do not contain adjuvant.

Most experts agree that worldwide use of IPV is preferable because of its proven protective track-record and safety. However, when compared to OPV, the cost-prize for IPV is significantly higher. This is mainly due to requirements for: (i) more virus per dose; (ii) additional downstream processing (i.e. concentration, purification and inactivation), and the related QC-testing (iii) loss of antigen or poor recovery in downstream and iv) containment. Until now, the financial challenge has been a major drawback for IPV innovation and implementation in low and middle-income countries. The production costs of sIPV are currently estimated equivalent to that for IPV, which is about 20-fold more expensive than OPV. The future global demand for IPV following eradication of polioviruses could increase from the current level of 80 million doses to 450 million doses per year. Consequently, approaches to "stretch" supplies of IPV are likely to be required.

Reduced-dose efficacious vaccine formulations which provide protection against infection using a lower dose of IPV antigen are desirable in situations where the supply of conventional vaccine is insufficient to meet global needs or where the cost of manufacture of the conventional vaccine prevents the vaccine being sold at a price which is affordable for developing countries. Also the exposure to lower dose of IPV; compared to the existing marketed formulations could be more safer. Thus, various strategies to make IPV available at more affordable prices need to be evaluated.

In case of pandemic influenza vaccines the use of adjuvants has permitted dose reduction, increased the availability and reduced cost of the vaccine. Therefore, it has been speculated that an adjuvanted vaccine formulation of sIPV would reduce cost and also increase the number of available sIPV doses worldwide.

Globally different research groups have been evaluating dose sparing for vaccines (Influenza vaccines in particular) by employing several adjuvants namely Alum, Emulsion, TLR-agonists (MPL, CpG, poly-IC, imiquimod), dmLT, 1,25-dihydroxyvitamin D3, CAF01, poly [di (carboxylato-phenoxy)-phosphazene] (PCPP) and Venezuelan equine encephalitis (VEE) replicon particles. Most of the adjuvant types being studied have encountered following hurdles i) Unknown safety or classified as toxic by regulatory agencies ii) having limitations regards to route of administration iii) lacking manufacturing reproducibility iv) stability of adjuvant.

Emulsion adjuvants (MF-59, AS03, AF3) have been previously reported to provide a strong dose-reduction effect (>30 fold) for Influenza and Hepatitis B vaccines. These adjuvants work by forming a depot at the site of injection, enabling the meted release of antigenic material and the stimulation of antibody producing plasma cells. However, these adjuvants have been deemed too toxic for widespread human prophylactic vaccine use and are usually reserved for those severe and/or terminal conditions such as cancer where there is a higher tolerance of side-effects.

Further, aluminium salts have been considered safe, are already being used in combination vaccines containing sIPV, have the lowest development hurdles and are inexpensive to manufacture. However aluminium adjuvants are not known for permitting significant dose-reduction.

One of the most critical steps in the production of vaccines against pathogens, in particular viral vaccines, is viral inactivation. In the case of virus inactivation, formalin is the most frequently used inactivating agent in the manufacture of vaccines. Formaldehyde inactivates a virus by irreversibly cross-linking primary amine groups in surface proteins with other nearby nitrogen atoms in protein or DNA through a —CH2-linkage. A potential problem with using formalin for viral inactivation is that this involves a series of chemical reactions that produce reactive products that can induce cross-linking of viral proteins and aggregation of virus particles. This could hamper the inactivating efficiency of the formalin and could also result in the partial destruction of the immunogenicity of the antigen in vaccine. Accordingly, it has been reported previously that formalin inactivation of polioviruses could affect the viral immunogenicity as well as antigenicity. Refer Morag Ferguson et al Journal of General Virology (1993), 74, 685-690. Most importantly, previously disclosed formaldehyde inactivation methods were particularly carried out in presence of phosphate buffer wherein significant D-antigen losses were observed along with epitope modification for Sabin Type I/II/III (D-antigen recovery post inactivation:22% for sabin type I, 15% for sabin type II, 25% for sabin type III), thereby failing to preserve the epitopic conformation. It is therefore possible that antibodies produced by recipients of formalin-inactivated polioviruses (in presence of phosphate buffer) may not contribute to the protective immune response.

By combining formalin and UV-inactivation, scientists tried to overcome the limitations of isolated UV-inactivation or formalin-inactivation, respectively, when inactivating the particularly resilient poliovirus. See, e.g., McLean, et al., "Experiences in the Production of Poliovirus Vaccines," Prog. Med. Virol., vol 1, pp. 122-164 (1958.) Taylor et al. (J. Immunol. (1957) 79:265-75) describe the inactivation of poliomyelitis virus with a formalin and ultraviolet combination. Molner et al. (Am. J. Pub. Health (1958) 48:590-8) describe the formation of a measurable level of circulating antibodies in the blood of subjects vaccinated with ultraviolet-formalin inactivated poliomyelitis vaccine. Truffelli et al. (Appl. Microbiol. (1967) 15:516-27) report on the inactivation of Adenovirus and Simian Virus 40 Tumorigenicity in hamsters by a three stage inactivation process consisting of formalin, UV light and β-propiolactone (BPL). Miyamae (Microbiol. Immunol. (1986) 30:213-23) describes the preparation of immunogens of Sendai virus by a treatment with UV rays and formalin. However previously discussed promising alternatives for formaldehyde like β-propiolactone (BPL) have been reported to produce an immune complex-reaction when combined with other components of the rabies vaccine. Additionally, it has been shown to produce squamous cell carcinomas, lymphomas and hepatomas in mice.

It is therefore particularly desirable to employ favorable formaldehyde inactivation conditions that maintain the structural integrity of antigenic structures of Sabin strains as well as utilize safe and cost-effective adjuvants that can result in significantly dose reduced (i.e. 8 to 10 fold) sIPV (Sabin IPV) vaccine compositions thereby reducing cost of manufacture, increasing vaccine supplies and making vaccines affordable for developing countries.

The present inventors have surprisingly found that D-antigen losses post-formaldehyde inactivation could be due to presence of phosphate buffer that unexpectedly causes undesirable aggregation of polio viruses. The instant invention provides an improved process of formaldehyde inactivation in presence of TRIS buffer thereby ensuring minimal epitopic modifications and subsequently minimizing D-antigen losses. Subsequently significantly dose reduced Sabin IPV vaccine compositions with at least 8 fold dose reduction for Sabin Type I and 3 fold dose reduction for Sabin Type III can be obtained.

SUMMARY OF THE INVENTION

One aspect of the application is directed to a dose reduced Inactivated Polio vaccine (IPV) composition. The composition includes an inactivated polio virus antigen selected from the group consisting of IPV Type 1 at a dose less than 15 D-antigen units (DU), IPV Type 2 at a dose less than 18 D-antigen unit (DU), and IPV Type 3 at a dose less than 17 D-antigen unit (DU), wherein the inactivated polio virus antigen is per 0.5 ml. The composition also includes one or more antigens selected from the group consisting of Diphtheria toxoid (D), Tetanus toxoid (T), Whole cell pertussis (wP), hepatitis B virus surface antigen (HBsAg), *Haemophilus influenzae* b PRP-Carrier protein conjugate (Hib), *Haemophilus influenzae* (a, c, d, e, f serotypes and the unencapsulated strains), *Neisseria meningitidis* A antigen(s), *Neisseria meningitidis* C antigen(s), *Neisseria meningitidis* W-135 antigen(s), *Neisseria meningitidis* Y antigen(s), *Neisseria meningitidis* X antigen(s), *Streptococcus Pneumoniae* antigen(s), *Neisseria meningitidis* B bleb or purified antigen (s), *Staphylococcus aureus* antigen(s), Anthrax, BCG, Hepatitis (A, C, D, E, F and G strains) antigen(s), Human papilloma virus, HIV *Salmonella typhi* antigen(s), acellular pertussis, modified adenylate cyclase, Malaria Antigen (RTS,S), Measles, Mumps, Rubella, Dengue, Zika, Ebola, Chikungunya, Japanese encephalitis, rotavirus, Diarrheal antigens, Flavivirus, smallpox, yellow fever, Shingles, and Varicella virus antigens.

Another aspect of the application is directed to a dose reduced Inactivated Polio vaccine (IPV) composition. The composition includes an inactivated polio virus antigen selected from the group consisting of IPV Type 1 at a dose less than 15 D-antigen units (DU), IPV Type 2 at a dose less than 18 D-antigen unit (DU), and IPV Type 3 at a dose less than 17 D-antigen unit (DU), wherein the inactivated polio virus is per 0.5 ml. The composition also includes a diphtheria toxoid, (D) antigen in an amount of 1 to 50 Lf per 0.5 ml, a tetanus toxoid, (T) antigen in an amount of 1 to 30 Lf per 0.5 ml, a whole cell pertussis, (wP) antigen in an amount of 1 to 50 IOU per 0.5 ml or acellular pertussis, (aP), a hepatitis B virus surface antigen, (HBsAg) in an amount of 1 to 20 ng per 0.5 ml, and a *Haemophilus influenzae* type b antigen, (Hib) in an amount of 1 to 20 ng per 0.5 ml.

Yet another aspect of the application is directed to a process of manufacturing a dose reduced Inactivated Polio vaccine (IPV) composition. The composition includes an inactivated polio virus antigen selected from the group consisting of IPV Type 1 at a dose less than 15 D-antigen units (DU), IPV Type 2 at a dose less than 18 D-antigen unit (DU), and IPV Type 3 at a dose less than 17 D-antigen unit (DU), per 0.5 ml. The composition also includes a diphtheria toxoid, (D) antigen in an amount of 1 to 50 Lf per 0.5 ml, a tetanus toxoid, (T) antigen in an amount of 1 to 30 Lf per 0.5 ml, a whole cell pertussis, (wP) antigen in an amount of 1 to 50 IOU per 0.5 ml or acellular pertussis, (aP) comprising one or more of modified adenylate cyclase, Pertussis toxoid (PT) 1-50 μg, Filamentous hemagglutinin (FHA) 1-50 μg, Pertactin (P69 or PRN) 1-20 μg or Fimbrial proteins (FIM 1, 2 and 3) 2-25n; per 0.5 ml, a hepatitis B virus surface antigen, (HBsAg) in an amount of 1 to 20 ng per 0.5 ml, and a *Haemophilus influenzae* type b antigen, (Hib) in an amount of 1 to 20 ng per 0.5 ml. The process comprises the steps of: a) adsorbing the IPV (Sabin/Salk strain) bulk individually on aluminium hydroxide, followed by pH adjustment to 6.2-6.6, more preferably 6.5; b) adsorbing the D on aluminium phosphate, followed by pH adjustment to 5.5-6.5; c) adsorbing the T on aluminium phosphate, followed by pH adjustment to 5.5-6.5; d) adsorbing the HBsAg on aluminium phosphate, followed by pH adjustment to 6.0-6.5; e) blending a mixture obtained from steps b), c), and d) by agitation at room temperature for 18-24 hours; f) blending a content of step (a) with the mixture obtained in steps b), c) and d), followed by pH adjustment to 6.4-6.6 and agitation at room temperature for 60 minutes; g) adding an inactivated wP antigen/acellular pertussis antigen and a stabilizer (Histidine amino acid buffer solution 100-300 mM) to the mixture in step f), followed by agitation for 60 minutes and left in static condition for overnight at 2-8° C.; h) adding the Hib antigen to the mixture obtained in step g) at 2-8° C., followed by pH adjustment to 6.4-6.6; and i) adjusting the pH to 6.0 to 7.0 with sodium hydroxide/sodium carbonate and adding normal saline (0.9% NaCl) or WFI (q.s.) to make up a volume of the mixture obtained in step h), followed by agitation for 2 hours.

Yet even another aspect of the application is directed to a method for producing a composition comprising Enteroviral poliovirus particles. The method includes the steps of: a) purifying the Enteroviral poliovirus particles in a medium comprising a phosphate buffer; b) exchanging the phosphate buffer of the purified Enteroviral poliovirus particles of step a) for a non-phosphate buffer selected from the group consisting of TRIS, TBS, MOPS, HEPES or bicarbonate buffer and a combination thereof; c) stabilizing the purified and buffer-exchanged Enteroviral poliovirus particles of step b); d) inactivating the Enteroviral poliovirus particles of step c) by: (i) adding formalin to the purified Enteroviral poliovirus particles and stirring for 7 days; (ii) filtering the product of step (i); and (iii) adding formalin to the product of step (ii) and stirring for 6 days; and (iv) filtering the product of step (iii). The non-phosphate buffer is present at a concentration of 30-70 mM. Aggregation of the Enteroviral poliovirus particles is prevented or reduced. The D-antigen losses are reduced post inactivation by 8 to 10 fold as compared to inactivation in phosphate buffer.

These aspects will be described in further detail below.

DETAILED DESCRIPTION

Figure 1:
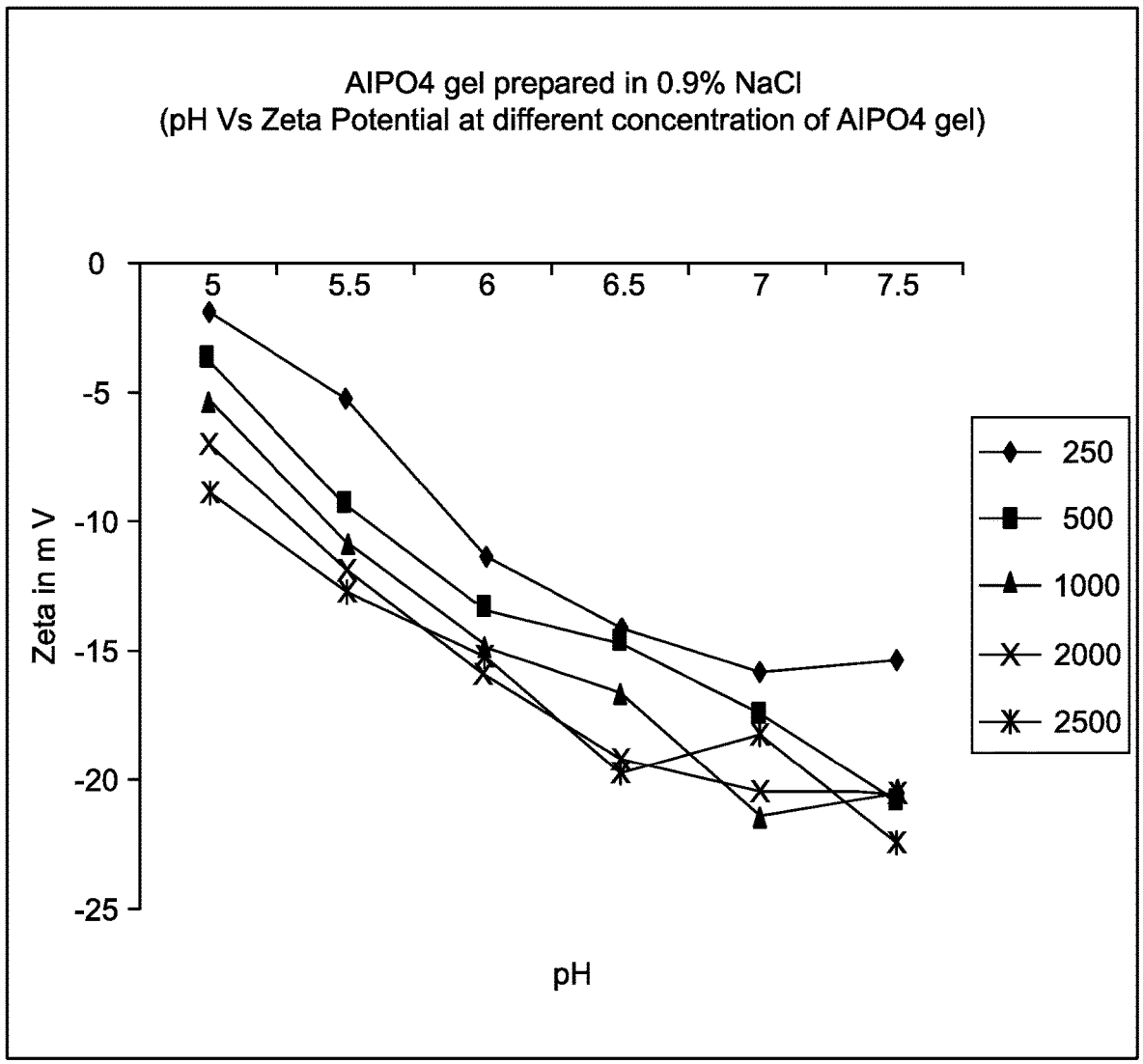
FIG. 1: Alum phosphate gel prepared in 0.9% NaCl (pH Vs Zeta potential at different concentrations of Alum phosphate gel).

Although the present disclosure may be susceptible to different embodiments, certain embodiments are shown in the following detailed discussion, with the understanding that the present disclosure can be considered an exemplification of the principles of the disclosure and is not intended to limit the scope of disclosure to that which is illustrated and disclosed in this description. Embodiments are provided so as to thoroughly and fully convey the scope of the present disclosure to the person skilled in the art. Numerous details are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known composition, well-known processes, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise.

The terms first, second, third, etc., should not be construed to limit the scope of the present disclosure as the aforementioned terms may be only used to distinguish one element, component, region, layer or section from another component, region, layer or section. Terms such as first, second, third etc., when used herein do not imply a specific sequence or order unless clearly suggested by the present disclosure.

The present disclosure provides an immunogenic composition and a process for preparing the same.

The term "vaccine" is optionally substitutable with the term "immunogenic composition" and vice versa.

"D-antigen units" (also referred to as "international units" or IU): The D antigenic form of the poliovirus induces protective neutralising antibodies. D antigen units referred to herein (for instance in the vaccines of the invention) are the measured total D antigen units of each unabsorbed bulk IPV antigen type prior to formulation of the final vaccine which are added in each human dose of formulated vaccine (typically 0.5 mL final volume). Reliable methods of measuring D-antigen units are well known in the art and are published, for instance, by the European Pharmacopoeia. For instance, D-antigen units may be measured using the ELISA test ("D-antigen quantification by ELISA") below. European Pharmacopoeia provides a test sample (European Pharmacopoeia Biological Reference Preparation—available from Ph. Eur. Secretariat, e.g. Code P 216 0000) for standardisation of such methods between manufacturers (Pharmeuropa Special Issue, Bio 96-2). Thus the D-antigen unit value is well understood in the art.

The term "dose" herein is typically one administration of the vaccine of the invention, which is typically one injection. A typical human dose is 0.5 mL. Of course various doses may be administered in a vaccine administration schedule.

The term "IPV" or an immunogenic composition comprising these components herein is intended to mean inactivated polio virus type 1 (e.g. Mahoney, as preferably used), type 2 (e.g. MEF-1), or type 3 (e.g. Saukett), or a Sabin Serotype 1, 2, 3 combination of either two or all three of these types. An example of a full (or standard) dose (40-8-32 D antigen units of Salk based IPV types 1, 2 and 3 respectively) IPV immunogenic composition for the purposes of this invention could be Poliovac® (Serum Institute of India Pvt. Ltd.). Thus, where it is stated herein that one, two, three fold dose reduction (reduced) as compared to standard dose of Salk based IPV is present in an immunogenic composition of the invention it is meant D-antigen units equating to X % of reduction of dose of 40, 8, and/or 32 D-antigen units of IPV types 1, 2 and/or 3 respectively (as measured in each bulk IPV antigen type) are formulated within each dose of said vaccine.

The term "saccharide" throughout this specification may indicate polysaccharide or oligosaccharide and includes both. The capsular saccharide antigen may be a full-length polysaccharide or it may be extended to bacterial 'sized-saccharides' and 'oligosaccharides' (which naturally have a low number of repeat units, or which are polysaccharides reduced in size for manageability, but are still capable of inducing a protective immune response in a host.

An important aspect of the instant invention is that said improved process of formalin inactivation and adsorption on alum salt comprises of following steps:

a) Adding Sabin IPV purified bulk to TRIS buffer (30 to 50 mM) having pH between 6.8 to 7.2, b) Adding M-199 medium containing glycine (5 gm/l) to mixture of (a), c) Adding 0.025% formaldehyde while mixing, d) Incubating mixture obtained in Step (c) at 37° C. from 5 to 13 days on magnetic stirrer, e) Subjecting post-incubation mixture to intermediate 0.22µ filtration on day 7 and final filtration on day 13, f) Storing bulk obtained after step (e) at 2-8° C., g) Performing D-Ag ELISA for D-Antigen unit determination, h) Taking the desired volume of autoclaved Al(OH)$_3$ to get the final concentration of Alum(Al$^{+++}$) between 0.8 to 1.2 mg/dose in a 50 ml Container, i) Adding IPV bulk with adjusted D-Ag unit and making up the volume with diluent (10× M-199+0.5 Glycine %), j) Adjusting the final formulation pH and obtaining final formulation with pH between 6 and 6.5, k) Subjecting the formulation bulk to magnetic stirring overnight at 2-8° C. and wherein formalin inactivation of step (a) does not occur in presence of phosphate buffer.

A first embodiment of instant invention is that said non-phosphate buffer to be used during formaldehyde inactivation can be selected from the group consisting of TRIS, TBS, MOPS, HEPES, and bicarbonate buffers.

A preferred aspect of first embodiment is that said formaldehyde inactivation can occur in presence of TRIS Buffer or TBS (TRIS Buffered saline) having concentration selected from 30 mM, 40 mM and 50 mM, preferably 40 mM and at a pH selected from 6.8, 6.9, 7, 7.1 and 7.2, preferably between 6.8 and 7.2 wherein said inactivation does not utilize any phosphate buffer.

A second embodiment of the instant invention is that adsorption of formalin inactivated sIPV can be done on aluminium hydroxide having concentration selected from 1.5 mg/dose, 1.8 mg/dose, 2.2 mg/dose, preferably between 2 mg/dose to 2.4 mg/dose and at a pH selected from 6.2, 6.3, 6.4 and 6.5, preferably 6.5.

A third embodiment of instant invention is that said improved process of formalin inactivation and aluminium hydroxide adsorption can result in D-Antigen recovery post-inactivation between 50% and 80% and percent adsorption of aluminium hydroxide can be between 85 and 99%.

One aspect of third embodiment is that present invention provides an improved process of formalin inactivation and aluminium hydroxide adsorption resulting in dose reduction of at least 8 fold for Sabin Type 1, at least 3 fold for Sabin Type 3 as compared to standard dose of 40 DU-8DU-32DU.

Second aspect of third embodiment is that instant invention provides improved formaldehyde inactivation and aluminium hydroxide adsorption methods that result in vaccine compositions comprising of i) inactivated poliovirus type 1 at a dose of at least SD-antigen units, ii) inactivated poliovirus type 2 at a dose of at least 8D-antigen units and iii) inactivated poliovirus type 3 at a dose of at least 10D-antigen units.

A fourth embodiment of instant invention is that said aluminium salt adjuvant is an aluminium hydroxide having concentration between 1.5 mg/0.5 ml dose and 2.5 mg/0.5 ml dose, preferably between 2.100 mg/0.5 ml dose and 2.4 mg/0.5 ml dose at a pH of about 6.5.

One aspect of fourth embodiment is that total aluminium content in the trivalent vaccine (Type 1, 2 and 3) can be between 800-1000 μg, preferably 800 μg Al$^{3+}$ per 0.5 mL dose, characterized in that at least 400 μg Al$^{3+}$ for Type 1, at least 200 μg Al$^{3+}$ for Type 2, at least 200 μg Al$^{3+}$ for Type 3.

Another aspect of fourth embodiment is that said dose reduced polio virus vaccine composition can consist of Type 1 and Type 3 and is devoid of Type 2 wherein the dose volume can be between 0.1 and 0.4 ml.

A fifth embodiment of instant invention is that the dose reduced vaccine compositions prepared by instant methods can be "Standalone sIPV" wherein the antigens may comprise of sIPV type 1 or sIPV type 2 or sIPV type 3, or sIPV types 1 and 2, or sIPV types 1 and 3, or sIPV types 2 and 3, or sIPV types 1, 2 and 3.

In first aspect of the fifth embodiment, Inactivated polio virus is selected from the group of Salk and Sabin strain; and the concentration of individual Type 1, Type 2, and Type 3 of Salk or Sabin strain based IPV is not more than 20 D antigen units.

In second aspect of the fifth embodiment, inactivated polio virus is a Salk strain and the concentration of individual Type 1, Type 2, or Type 3 of Salk strain based IPV is selected from the group of dose composition comprising of 7.5-16-10, 8-2-5, 10-2-5, 10-2-10, 10-2-12, 10-2-16, 7.5-16-10, 5-2-5 D antigen units; more particularly concentration of individual Type 1, Type 2, or Type 3 of Salk strain based IPV is selected from group of 8-2-5 and 10-2-10 D antigen units.

In third aspect of the fifth embodiment, inactivated polio virus is a Sabin strain and the concentration of individual Type 1, Type 2, and Type 3 of Sabin strain based IPV is selected from the group of dose composition comprising of 5-16-10, 2.5-8-5, 5-8-10 D antigen units; more particularly concentration of individual Type 1, Type 2, and Type 3 of Sabin strain based IPV is 5-16-10 D antigen units.

A sixth embodiment of instant invention is that the dose reduced vaccine compositions prepared by instant methods can be "Combination Vaccines containing dose reduced IPV" wherein said non-IPV antigens of combination vaccines can be selected from but not limited to Diphtheria toxoid (D), Tetanus toxoid (T), Whole cell pertussis (wP), hepatitis B virus surface antigen (HBsAg), *Haemophilus influenzae* b PRP-Carrier protein conjugate (Hib), *Haemophilus influenzae* (a, c, d, e, f serotypes and the unencapsulated strains), *Neisseria meningitidis* A antigen(s), *Neisseria meningitidis* C antigen(s), *Neisseria meningitidis* W-135 antigen(s), *Neisseria meningitidis* Y antigen(s), *Neisseria meningitidis* X antigen(s), *Streptococcus Pneumoniae* antigen(s), *Neisseria meningitidis* B bleb or purified antigen(s), *Staphylococcus aureus* antigen(s), Anthrax, BCG, Hepatitis (A, C, D, E, F and G strains) antigen(s), Human papilloma virus, HIV *Salmonella typhi* antigen(s), acellular pertussis, modified adenylate cyclase, Malaria Antigen (RTS,S), Measles, Mumps, Rubella, Dengue, Zika, Ebola, Chikungunya, Japanese encephalitis, rotavirus, Diarrheal antigens, Flavivirus, smallpox, yellow fever, Shingles, Varicella virus antigens.

A preferred aspect of the sixth embodiment, wherein the Combination Vaccines comprising dose reduced IPV may comprise of antigens selected from Diphtheria toxoid (D), Tetanus toxoid (T), Whole cell pertussis (wP), acellular pertussis, hepatitis B virus surface antigen (HBsAg), *Haemophilus influenzae* b PRP-Carrier protein conjugate (Hib) other than dose reduced IPV as disclosed in earlier embodiment.

A preferred aspect of the sixth embodiment is that the Combination Vaccines comprising dose reduced IPV may comprise of IPV type 1 or IPV type 2 or IPV type 3, or IPV type 1 and 2, or IPV type 1 and 3, or IPV type 2 and 3, or IPV type 1, 2 and 3.

In preferred aspect of the sixth embodiment, inactivated polio virus is a Salk strain and the concentration of individual Type 1, Type 2, or Type 3 of Salk strain based IPV is selected from the group of dose composition comprising of 7.5-16-10, 8-2-5, 10-2-5, 10-2-10, 10-2-12, 10-2-16, 7.5-16-10, 5-2-5 D antigen units; more particularly concentration of individual Type 1, Type 2, or Type 3 of Salk strain based IPV is selected from group of 8-2-5 and 10-2-10 D antigen units.

In preferred aspect of the sixth embodiment, inactivated polio virus is a Sabin strain and the concentration of individual Type 1, Type 2, and Type 3 of Sabin strain based IPV is selected from the group of dose composition comprising of 5-16-10, 2.5-8-5, 5-8-10 D antigen units; more particularly concentration of individual Type 1, Type 2, and Type 3 of Sabin strain based IPV is 5-16-10 D antigen units.

Components of the Combination Vaccine Composition:

Inactivated Polio Virus (IPV)

Polio (Poliomyelitis) is a highly infectious virus. The poliovirus invades the nervous system and can cause irreversible paralysis in a matter of hours. Three types of poliovirus exist globally i.e. Type 1, Type 2, & Type 3.

Seventh embodiment of the present invention comprises of improved methods of Polio virus (salk or sabin strains) inactivation by formaldehyde in presence of Non-Phosphate Buffer (TRIS, TBS, MOPS, HEPES, and bicarbonate) resulting in maximum recovery of D-antigen. Subsequent adsorption of said IPV on aluminium hydroxide provides significantly dose reduced IPV compositions. The instant invention provides an improved process of formalin inactivation and aluminium hydroxide adsorption, wherein the D-Antigen recovery post-inactivation is in the range of 50-80% and percent adsorption of aluminium hydroxide is in the range of 70-99%.

In one of the aspects of the seventh embodiment, CCL81-VERO (Monkey kidney) cell were used as host cells for the growing of polio virus i.e. Sabin and Salk strains. After infection of host cells with desired strain of polio virus and incubation of 72 hours, the medium containing the virus and cell debris was pooled and collected in a single container.

In second aspect of the seventh embodiment, the harvest may be subjected to series of filtration (6μ and 0.45μ assembly); and filtrate was collected in a glass container. The filtrate was subjected to tangential flow filtration with 100 kDa cassette; diafiltered using phosphate buffer and purified using anion exchange chromatography.

In third aspect of the seventh embodiment, the purified virus pool may be further subjected to buffer exchange from Phosphate buffer to Non-Phosphate Buffer (TRIS, TBS, MOPS, HEPES, and bicarbonate) (30 to 70 mM, pH: 7-7.5) with TFF system (100 kDa, 0.1 $m^2$) followed by addition of M-199 and 0.1-1.0% glycine.

In fourth aspect of the seventh embodiment purified virus pool in Non-Phosphate Buffer (TRIS, TBS, MOPS, HEPES, and bicarbonate) (30 to 70 mM, pH: 7-7.5) was subjected to inactivation by 0.01-1.0% formalin with continuous stirring of virus bulk and incubated at ambient temperature for 13 days, with intermediate filtration on day 7. Further, the inactivated bulk was subjected to final filtration and later stored at 2-8° C.

In fifth aspect of the seventh embodiment, final purified bulk may be subjected to adsorption on $Al(OH)_3$, wherein the final alum ($Al^{3+}$) concentration is between 0.1-1.5 mg/dose, M-199+0.5% glycine was used to make up the volume and pH was adjusted to 6-7 using 1N HCl/NaOH, further subjected to overnight stirring at 2-8° C.

The present inventors have surprisingly observed that D-antigen loss, post-formaldehyde inactivation was due to presence of phosphate buffer that unexpectedly causes undesirable aggregation of polio viruses. The instant invention provides an improved process of formaldehyde inactivation in presence of Non-Phosphate Buffer (TRIS, TBS, MOPS, HEPES, and bicarbonate) (30 to 70 mM, pH: 7-7.5) thereby ensuring minimal epitopic modifications and subsequently minimizing D-antigen loss.

*Haemophilus influenzae* b (Hib) PRP—Protein Conjugate:

*Haemophilus influenzae* type b is a Gram-negative bacterium that causes meningitis and acute respiratory infections, mainly in children. The outermost structure of *H. influenzae* type b is composed of polyribosyl-ribitol-phosphate (PRP), a polysaccharide that is responsible for virulence and immunity. PRP is a hapten which is considered as poor immunogenic in nature hence PRP is linked covalently with a carrier protein to make highly immunogenic Hib antigen. This process changes the polysaccharide from a T-independent to a T-dependent antigen and greatly improves immunogenicity, particularly in young children.

Eighth embodiment of the present invention comprises of preparation of Hib PRP-protein conjugate. It may be noted that the carrier proteins used for the conjugation of the Hib antigen may be selected from group comprising of Tetanus toxoid, $CRM_{197}$ (Cross Reactive Material 197, a genetically detoxified form of diphtheria toxoid), Diphtheria toxoid, *Neisseria meningitidis* outer membrane complex, fragment C of tetanus toxoid, pertussis toxoid, protein D of *H. influenzae, E. coli* LT, *E. coli* ST, and exotoxin A from *Pseudomonas aeruginosa*, outer membrane complex c (OMPC), porins, transferrin binding proteins, pneumolysin, pneumococcal surface protein A (PspA), pneumococcal surface adhesin A (PsaA), pneumococcal PhtD, pneumococcal surface proteins BVH-3 and BVH-11, protective antigen (PA) of *Bacillus anthracis* and detoxified edema factor (EF) and lethal factor (LF) of *Bacillus anthracis*, ovalbumin, keyhole limpet hemocyanin (KLH), human serum albumin, bovine serum albumin (BSA) and purified protein derivative of tuberculin (PPD), synthetic peptides, heat shock proteins, pertussis proteins, cytokines, lymphokines, hormones, growth factors, artificial proteins comprising multiple human CD4+ T cell epitopes from various pathogen-derived antigens such as N 19, iron-uptake proteins, toxin A or B from *C. difficile* and *S. agalactiae* proteins or any equivalents thereof. Preferably the carrier protein in conjugate is selected from TT or $CRM_{197}$.

In first aspects of the eighth embodiment, Hib antigen may be derived from the capsular polysaccharide of *Haemophilus influenzae* type b strain. To produce the PRP polysaccharide, *H. Influenzae* type-b bacteria was grown in semi synthetic media under certain conditions of temperature, agitation and optical density etc. PRP is an outer membrane bound polysaccharide, gets released into the medium during the fermentation under agitation condition. Fermented biomass separated broth contains crude PRP, which was again purified by precipitation using a detergent N,N, N-trimethyl-1-hexadecanaminium bromide, followed by ethanol gradient precipitation and filtration. Final purified PRP polysaccharide was tested for meeting the specifications like endotoxin, nucleic acid and protein as per the WHO, BP, EP, IP etc.

In second aspect of the eighth embodiment, polysaccharide—protein conjugate may be prepared by coupling of polysaccharide (PRP) with a carrier protein. Hib PRP was conjugated to carrier protein using conjugation process comprising of steps including depolymerization of PRP using alkaline buffer to achieve size reduced PRP; treatment with a cyanylation agent like CDAP (1-cyano-4-dimethylamino pyridinium tetrafluoroborate) to form a cyanate ester;

coupling of activated cyanylated polysaccharide to amino group of carrier protein; purification of final conjugate using ultrafiltration.

More preferably, the optimal input ratio of reactants i.e. PRP, CDAP and $CRM_{197}$ may be selected at 1:1.5:1 ratio for conjugation reaction. During conjugation, purified PRP polysaccharide was depolymerized using an alkaline buffer (0.4M Carb-Bicarbonate buffer, pH 10.5±0.1) to achieve size reduced PRP. Size reduced PRP was treated for cyanylation using CDAP (1-cyano-4-dimethylamino pyridinium tetrafluoroborate) chemistry to form a cyanate ester. The activated cyanylated polysaccharide was coupled directly with amino group on the carrier protein $CRM_{197}$. The degree of conversion of Hib conjugate was confirmed by the offline testing using HPLC. The conjugation reaction was quenched by achieving the desired level of conversion of conjugate with the specification of not less than 65% conversion of Hib conjugate, and then conjugate reaction was neutralized by Glycine (2M) addition. The Hib PRP-$CRM_{197}$ Conjugate was further purified on ultra-filtration membrane filters (300 kDa and 100 kDa) to remove nonreactive reagents and byproducts. Final conjugate bulk is 0.22 µm filtered and stored at 2-8° C.

More preferably, Hib PRP may be conjugated to carrier protein wherein the saccharide: protein ratio (w/w) may be between 0.4 and 1; and the free PRP content in final Hib PRP—protein conjugate bulk may be not more than 5%, more preferably is less than 2%.

In third aspect of the eighth embodiment, the Hib PRP may be conjugated to tetanus toxoid (TT) by CNBr chemistry, Reductive amination chemistry, Cyanylation chemistry or any other chemistry already discloses in Kniskern et al., "Conjugation: design, chemistry, and analysis" in Ellis et al., Development and clinical uses of *Haemophilus influenzae* type B conjugate vaccines. New York: Marcel Dekker, 1994: 37-69

In forth aspect of the eighth embodiment, the carrier protein may be present in both free and conjugated form in a composition of the present disclosure, the unconjugated form is preferably no more than 20% of the total amount of the carrier protein in the composition as a whole, and more preferably present at less than 5% by weight, more preferably is less than 2%.

In fifth aspect of the eighth embodiment, the Hib antigen is not substantially adsorbed on to any adjuvant.

In sixth aspect of the eighth embodiment, the Hib antigen may not be subjected to deliberate or intentional adsorption on any adjuvant.

In seventh aspect of the eighth embodiment, the percentage of adsorption of Hib antigen on to any adjuvant may be less than 20%.

In eighth aspect of the eighth embodiment, the Hib antigen used in the combination vaccine of the present disclosure is derived from the capsular polysaccharide of *Haemophilus influenzae* type b (Hib) strain 760705.

Diphtheria Toxoid

Diphtheria is an infectious disease caused by the bacterium *Corynebacterium diphtheria*, which primarily infects the throat and upper airways, and produces a toxin affecting other organs. Diphtheria toxin is an exotoxin secreted by *Corynebacterium diphtheria*, possesses antigenic properties and is toxic in nature. To reduce toxicity, the toxin is converted to the inactive toxoid by subjecting it to inactivation. The inactivation process may be selected from one or more of treatment with Heat, UV, Formalin/Formaldehyde, Acetylethyleneimine, etc. To increase immunogenicity, the toxoid is adsorbed to an adjuvant. The toxoid thus formed is able to induce anti toxin antibodies against *C. diphtheria*. Existence of dimers can lead to adverse reactions.

In ninth embodiment of the present invention, Diphtheria toxoid was prepared.

In first aspect of the ninth embodiment, diphtheria toxin (exotoxin) may be obtained from *Corynebacterium diphtheria* and detoxified using a suitable inactivating agent. The example of suitable inactivating agent includes Formaldehyde.

In second aspect of the ninth embodiment, diphtheria toxoid obtained may be purified using Gel filtration chromatography with Sephacryl S-300 HR as resin with linear flow rate of 2-5 ml/min and stabilized by addition of an amino acid buffer solution (Histidine, lysine, glycine, arginine) or polysorbate solution at a final concentration of 5-300 mM, and stored at temperature −20 to +40° C. till further use. The purified D thus obtained comprises of homogenous fraction devoid of undesirable aggregates (Refer FIG. 1) with at least 80-90% monomeric diphtheria toxoid further used for formulation of multivalent vaccine(s). Further PLgel, Sephacryl S-200HR, Sephadex, Bio-Gel (cross linked polyacrylamide), agarose gel and/or Styragel may also be used for the purpose of purification using Gel permeation chromatography. The purified diphtheria toxoid is stabilized by addition of Histidine (200 mM) amino acid buffer solution.

In third aspect of the ninth embodiment, diphtheria toxoid may be adsorbed on to adjuvant selected from the group of aluminium salt ($Al^{3+}$) such as aluminium hydroxide ($Al(OH)_3$) or aluminium phosphate ($AlPO_4$), alum, calcium phosphate, MPLA, 3D-MPL, QS21, a CpG-containing oligodeoxynucleotide adjuvant, liposome, or oil-in-water emulsion or a combination thereof.

Yet preferably diphtheria toxoid may be adsorbed on to aluminium salt including aluminium hydroxide and aluminium phosphate, preferably on Alum phosphate.

Yet preferably the Diphtheria toxoid (D) antigen may be adsorbed on to aluminium phosphate having percentage adsorption of at least 50%.

Tetanus Toxoid (T)

Tetanus is an acute infectious disease caused by toxigenic strains of the bacterium *Clostridium tetani* (*C. tetani*), a gram-positive, spore-forming, strictly anaerobic bacterium. Tetanus toxin is an exotoxin secreted by *Clostridium tetani*, possesses antigenic properties and is toxic in nature. To reduce toxicity, the toxin is converted to the inactive toxoid by subjecting it to inactivation. The inactivation process may be selected from one or more of treatment with Heat, UV, Formalin/Formaldehyde, Acetylethyleneimine, etc. To increase immunogenicity, the toxoid is adsorbed to an adjuvant. The toxoid thus formed is able to induce anti toxin antibodies against *Clostridium tetani*. Existence of dimers can lead to adverse reactions.

In tenth embodiment of the present invention, Tetanus toxoid was prepared.

In first aspect of the tenth embodiment, Tetanus toxin may be obtained from *Clostridium tetani* and detoxified using a suitable inactivating agent. The example of suitable inactivating agent includes Formaldehyde.

In second aspect of the tenth embodiment, Tetanus toxoid obtained may be purified using Gel filtration chromatography with Sephacryl S-300 HR as resin with linear flow rate of 2-5 ml/min and stabilized by addition of an amino acid buffer solution (Histidine, lysine, glycine, arginine) or polysorbate solution at a final concentration of 5-300 mM, and stored at temperature −20 to +40° C. till further use. The purified T thus obtained was a homogenous fraction devoid of undesirable aggregates with at least 80-90% monomeric tetanus toxoid further used for formulation of multivalent vaccine. Further PLgel, Sephacryl S-200HR, Sephadex, Bio-Gel (cross-linked polyacrylamide), agarose gel and Styragel may also be used for the purpose of purification using Gel permeation chromatography. The purified tetanus toxoid is stabilized by addition of Histidine (200 mM) amino acid buffer solution.

In third aspect of the tenth embodiment, Tetanus toxoid may be adsorbed on to adjuvant selected from the group of aluminium salt ($Al^{3+}$) such as aluminium hydroxide (Al(OH)$_3$) or aluminium phosphate (AlPO$_4$), alum, calcium phosphate, MPLA, 3D-MPL, QS21, a CpG-containing oligodeoxynucleotide adjuvant, liposome, or oil-in-water emulsion or a combination thereof.

Yet preferably tetanus toxoid may be adsorbed on to aluminium salt including aluminium hydroxide and Aluminium phosphate, preferably on Alum phosphate.

Yet preferably the tetanus toxoid (T) antigen may be adsorbed on to aluminium phosphate having percentage adsorption of at least 40%.

Pertussis Antigen

Pertussis (whooping cough) is caused by *Bordetella pertussis*, a small Gram-negative coccobacillus that infects the mucosal layers of the human respiratory tract. Two forms of vaccine are in use, the whole-cell pertussis vaccine (wP), and the acellular pertussis vaccine (aP). Whole-cell pertussis vaccines are suspensions of the entire *B. pertussis* organism that has been inactivated, usually with formalin. Immunization with wP vaccine is relatively inexpensive and highly effective. Also, presence of wP in combination vaccines acts as an adjuvant for many other antigenic component.

Acellular pertussis (aP) vaccines contain purified components of *B. pertussis* such as inactivated pertussis toxin either alone or in combination with other *B. pertussis* components such as filamentous haemagglutinin, fimbrial antigens, pertactin, and modified adenylate cyclase more particularly a non-cytotoxic polypeptide, derived from the adenylate cyclase protein (CyaA-derived polypeptide) of a *Bordetella pertussis*. Acellular pertussis vaccine offers less adverse reaction as compared to wP vaccine.

In eleventh embodiment of the present invention, the pertussis vaccine is pertussis antigen selected from one or more of whole cell pertussis or acellular pertussis.

In first aspect of the eleventh embodiment, pertussis vaccine is an acellular pertussis antigen selected from one or more of filamentous haemagglutinin, fimbrial antigens, pertactin, and modified adenylate cyclase more particularly a non-cytotoxic polypeptide, derived from the adenylate cyclase protein (CyaA-derived polypeptide) of a *Bordetella pertussis*. Acellular pertussis antigens may be expressed in suitable host using recombinant DNA technology.

Preferably acellular pertussis antigen may be selected from—*Bordetella* toxin in detoxified form (in particular either genetically or chemically detoxified), in particular Pertussis toxin; Filamentous Haemagglutinin; Pertactin; or Fimbriae. Particularly Pertussis toxoid: 1 to 50 micrograms (More particularly 8 μg); —Filamentous Haemagglutinin: 1 to 50 micrograms (More particularly 8 μg); —Pertactin: 1 to 20 micrograms (More particularly 2.5 μg); —Optionally, Fimbriae: 2 to 25 micrograms; per 0.5 ml.

In second aspect of the eleventh embodiment, pertussis vaccine is a whole cell pertussis comprising of *Bordetella pertussis* strains 134, 509, 25525 and 6229 in a specific ratio and subsequently inactivated by utilizing improved methods of inactivation devoid of thimerosal; hence leading to reduced reactogenicity and increased potency. Preferably, wP antigen is made from *Bordetella pertussis* strains 134, 509, 25525 and 6229 mixed in a ratio of 1:1:0.25:0.25.

In third aspect of the eleventh embodiment, wP inactivation process includes heat inactivation at 56±2° C. for 10 to 15 minutes in presence of formaldehyde; wherein wP bulk remains non-clumpy and easily homogenized thereby leading to reduced reactogenicity and giving better wP potency for a longer duration.

Hepatitis B Surface Antigen (HBsAg)

Hepatitis B is a potentially life-threatening liver infection caused by the Hepatitis B virus (HBV). Hepatitis B surface antigen (HBsAg) is a surface protein that also acts as an immunogen in highly effective vaccines for prevention of HBV infection. HBsAg protein can be recombinantly expressed in a suitable host microorganism; or can be isolated from the blood plasma of a chronic Hepatitis B patient/carrier.

In twelfth embodiment of the present invention, Hepatitis B surface antigen (HBsAg) was prepared.

In one of the aspect of twelfth embodiment, HBsAg was expressed in *Hansenula polymorpha* yeast cells using recombinant DNA technology. Other yeasts such as *Saccharomyces cerevisiae* may also be used as host cell for recombinant expression of HBsAg.

In one of the aspect of twelfth embodiment, Hepatitis B antigen (HBsAg) may be adsorbed on to adjuvant selected from the group of aluminium salt ($Al^{3+}$) such as aluminium hydroxide (Al(OH)$_3$) or aluminium phosphate (AlPO$_4$), alum, calcium phosphate, MPLA, 3D-MPL, QS21, a CpG-containing oligodeoxynucleotide adjuvant, liposome, or oil-in-water emulsion or a combination thereof.

Yet preferably Hepatitis B antigen (HBsAg) may be adsorbed on to Aluminium salt including Aluminium hydroxide and Aluminium Phosphate, preferably on Alum phosphate.

Yet preferably the Hepatitis B surface antigen (HBsAg) may be adsorbed on to aluminium phosphate having percentage adsorption of at least 70%.

In thirteenth embodiment of the present disclosure, the process for preparation of combination vaccine composition/formulation comprising Dose reduced IPV is disclosed.

One of the preferred aspects of thirteenth embodiment, wherein the process for preparation of Combination Vaccine Compositions comprising Dose reduced IPV, HBs, D, T, wP, and Hib PRP—Protein conjugate is as given below:

a) adsorbing IPV (Sabin/Salk strain) bulk individually on Aluminium hydroxide, followed by pH adjustment to 6.2-6.6, more preferably 6.5.

b) adsorbing D on Aluminium phosphate, followed by pH adjustment to 5.5-6.5 c) adsorbing T on Aluminium phosphate, followed by pH adjustment to 5.5-6.5 d) adsorbing HBsAg on Aluminium phosphate, followed by pH adjustment to 6.0-6.5.

e) blending the mixture as obtained in step (b), (c), (d) by agitation at room temperature for 18-24 hours.

f) Blending the mixtures as obtained in step (a) and (e), followed by pH adjustment to 6.4-6.6 and agitation at room temperature for 60 minutes.

g) adding inactivated wP antigen/acellular pertussis antigen and a stabilizer more preferably amino acid buffer solution (Histidine 100-300 mM) to the above mixture in step (f), followed by agitation for 60 minutes and left in static condition for overnight at 2-8° C.

h) adding Hib antigen to the mixture obtained in step (g) at 2-8° C., followed by pH adjustment to 6.4-6.6.

i) Adjusting pH to 6.0 to 7.0 with Sodium Hydroxide/ Sodium Carbonate and adding normal saline (0.9% NaCl) or WFI (q.s.) to make up the volume of the mixture obtained in step h, followed by agitation for 2 hours.
j) The process may further comprise of adding preservative to the mixture obtained in step (h) selected from:
  i. 2-Phenoxyethanol in an amount of 1 to 6 mg per 0.5 ml (v/v) and methylparaben in an amount of 0.1-1.5 mg per 0.5 ml (w/v); or
  ii. 2-Phenoxyethanol in an amount of 1 to 6 mg per 0.5 ml (v/v) and propylparaben in an amount of 0.05-0.2 mg per 0.5 ml (w/v); or
  iii. 2-Phenoxyethanol in an amount of 1 to 6 mg per 0.5 ml (v/v), methylparaben in an amount of 0.1-1.5 mg per 0.5 ml (w/v) and propylparaben in an amount of 0.05-0.2 mg per 0.5 ml (w/v);
  iv. 2-phenoxyethanol in an amount of 1 to 6 mg (v/v) per 0.5 ml as preservative.

In fourteenth embodiment of the present disclosure, the combination vaccine composition/formulation comprising Dose reduced IPV is an all liquid hexavalent vaccine formulation comprising of:

TABLE 1

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 1-50 Lf | Preferably one of 10 or 22.5 or 25 Lf |
| 2 | Tetanus toxoid (T) | 1-30 Lf | Preferably one of 2 or 7.5 or 10 Lf |
| 3 | Inactivated B. pertussis antigen (wP) | 1-50 IOU | Preferably one of 12 or 15 or 16 IOU |
| 4 | HBs antigen | 1-20 µg | Preferably one of 8 or 10 or 12.5 µg |
| 5 | Hib PRP-TT conjugate antigen | 1-20 µg of PRP | Preferably one of 8 or 10 or 13 µg of PRP |
| Inactivated Polio Virus (IPV) Sabin Serotype | | | |
| 6 | Type 1 (D antigen units) | 1-20 DU | 5 DU |
|   | Type 2 (D antigen units) | 1-20 DU | 16 DU |
|   | Type 3 (D antigen units) | 1-20 DU | 10 DU |
| 7 | Total Aluminium Content ($Al^{3+}$) | 0.1-1.2 mg | Preferably NMT 0.3 or NMT 0.55 or NMT 0.9 |
| 8 | 2-Phenoxyethanol | 1-6 mg | Preferably one of 2 or 2.5 or 3.25 mg |
| 9 | L-Histidine | 0.1-5 mg | Preferably one of 0.7 or 1 or 1.55 mg |

NMT—Not more than

In fifteenth embodiment of the present disclosure, the combination vaccine composition/formulation comprising Dose reduced IPV is an all liquid hexavalent vaccine formulation comprising of:

TABLE 2

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 1-50 Lf | Preferably one of 10 or 22.5 or 25 Lf |
| 2 | Tetanus toxoid (T) | 1-30 Lf | Preferably one of 2 or 7.5 or 10 Lf |
| 3 | Inactivated B. pertussis antigen (wP) | 1-50 IOU | Preferably one of 12 or 15 or 16 IOU |
| 4 | HBs antigen | 1-20 µg | Preferably one of 8 or 10 or 12.5 µg |
| 5 | Hib PRP-TT conjugate antigen | 1-20 µg of PRP | Preferably one of 8 or 10 or 13 µg of PRP |
| Inactivated Polio Virus (IPV) Sabin Serotype | | | |
| 6 | Type 1 (D antigen units) | 1-20 DU | 2.5 DU |
|   | Type 2 (D antigen units) | 1-20 DU | 8 DU |
|   | Type 3 (D antigen units) | 1-20 DU | 5 DU |
| 7 | Total Aluminium Content ($Al^{3+}$) | 0.1-1.2 mg | Preferably NMT 0.3 or NMT 0.55 or NMT 0.9 |
| 8 | 2-Phenoxyethanol | 1-6 mg | Preferably one of 2 or 2.5 or 3.25 mg |
| 9 | L-Histidine | 0.1-5 mg | Preferably one of 0.7 or 1 or 1.55 mg |

NMT—Not more than

In sixteenth embodiment of the present disclosure, the combination vaccine composition/formulation comprising Dose reduced IPV is an all liquid hexavalent vaccine formulation comprising of:

TABLE 3

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 1-50 Lf | Preferably one of 10 or 22.5 or 25 Lf |
| 2 | Tetanus toxoid (T) | 1-30 Lf | Preferably one of 2 or 7.5 or 10 Lf |
| 3 | Inactivated B. pertussis antigen (wP) | 1-50 IOU | Preferably one of 12 or 15 or 16 IOU |
| 4 | HBs antigen | 1-20 µg | Preferably one of 8 or 10 or 12.5 µg |
| 5 | Hib PRP-TT conjugate antigen | 1-20 µg of PRP | Preferably one of 8 or 10 or 13 µg of PRP |
|  | Inactivated Polio Virus (IPV) Sabin Serotype | | |
| 6 | Type 1 (D antigen units) | 1-20 DU | 7.5 DU |
|  | Type 2 (D antigen units) | 1-20 DU | 16 DU |
|  | Type 3 (D antigen units) | 1-20 DU | 10 DU |
| 7 | Total Aluminium Content ($Al^{3+}$) | 0.1-1.2 mg | Preferably NMT 0.3 or NMT 0.55 or NMT 0.9 |
| 8 | 2-Phenoxyethanol | 1-6 mg | Preferably one of 2 or 2.5 or 3.25 mg |
| 9 | L-Histidine | 0.1-5 mg | Preferably one of 0.7 or 1 or 1.55 mg |

NMT—Not more than

In seventeenth embodiment of the present disclosure, the combination vaccine composition/formulation comprising Dose reduced IPV is an all liquid hexavalent vaccine formulation comprising of:

TABLE 4

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 1-50 Lf | Preferably one of 10 or 22.5 or 25 Lf |
| 2 | Tetanus toxoid (T) | 1-30 Lf | Preferably one of 2 or 7.5 or 10 Lf |
| 3 | Inactivated *B. pertussis* antigen (wP) | 1-50 IOU | Preferably one of 12 or 15 or 16 IOU |
| 4 | HBs antigen | 1-20 µg | Preferably one of 8 or 10 or 12.5 µg |
| 5 | Hib PRP-TT conjugate antigen | 1-20 µg of PRP | Preferably one of 8 or 10 or 13 µg of PRP |
| 6 | Inactivated Polio Virus (IPV) Salk Serotype | | |
|  | Mahoney Type 1 (D antigen units) | 1-20 DU | 7.5 DU |
|  | MEF-1 Type 2 (D antigen units) | 1-20 DU | 16 DU |
|  | Saukett Type 3 (D antigen units) | 1-20 DU | 10 DU |
| 7 | Total Aluminium Content ($Al^{3+}$) | 0.1-1.2 mg | Preferably NMT 0.3 or NMT 0.55 or NMT 0.9 |
| 8 | 2-Phenoxyethanol | 1-6 mg | Preferably one of 2 or 2.5 or 3.25 mg |
| 9 | L-Histidine | 0.1-5 mg | Preferably one of 0.7 or 1 or 1.55 mg |

NMT—Not more than

In eighteenth embodiment of the present disclosure, the combination vaccine composition/formulation comprising Dose reduced IPV is an all liquid hexavalent vaccine formulation comprising of:

TABLE 5

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 1-50 Lf | Preferably one of 10 or 22.5 or 25 Lf |
| 2 | Tetanus toxoid (T) | 1-30 Lf | Preferably one of 2 or 7.5 or 10 Lf |
| 3 | Inactivated *B. pertussis* antigen (wP) | 1-50 IOU | Preferably one of 12 or 15 or 16 IOU |
| 4 | HBs antigen | 1-20 µg | Preferably one of 8 or 10 or 12.5 µg |
| 5 | Hib PRP-TT conjugate antigen | 1-20 µg of PRP | Preferably one of 8 or 10 or 13 µg of PRP |

TABLE 5-continued

| Sr. No. | Formulation Components | Antigen Unit/0.5 ml Dose | Preferred Antigen Unit/0.5 ml Dose (In any of the combination) |
|---|---|---|---|
| 6 | Inactivated Polio Virus (IPV) Salk Serotype | | |
|  | Mahoney Type 1 (D antigen units) | 1-20 DU | 8 DU |
|  | MEF-1 Type 2 (D antigen units) | 1-20 DU | 2 DU |
|  | Saukett Type 3 (D antigen units) | 1-20 DU | 5 DU |
| 7 | Total Aluminium Content ($Al^{3+}$) | 0.1-1.2 mg | Preferably NMT 0.3 or NMT 0.55 or NMT 0.9 |
| 8 | 2-Phenoxyethanol | 1-6 mg | Preferably one of 2 or 2.5 or 3.25 mg |
| 9 | L-Histidine | 0.1-5 mg | Preferably one of 0.7 or 1 or 1.55 mg |

NMT—Not more than

In nineteenth embodiment of the present disclosure, the combination vaccine composition/formulation comprising Dose reduced IPV is an all liquid hexavalent vaccine formulation comprising of:

TABLE 6

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 1-50 Lf | Preferably one of 10 or 22.5 or 25 Lf |
| 2 | Tetanus toxoid (T) | 1-30 Lf | Preferably one of 2 or 7.5 or 10 Lf |
| 3 | Inactivated *B. pertussis* antigen (wP) | 1-50 IOU | Preferably one of 12 or 15 or 16 IOU |
| 4 | HBs antigen | 1-20 µg | Preferably one of 8 or 10 or 12.5 µg |
| 5 | Hib PRP-TT conjugate antigen | 1-20 µg of PRP | Preferably one of 8 or 10 or 13 µg of PRP |
| 6 | Inactivated Polio Virus (IPV) Salk Serotype | | |
|  | Mahoney Type 1 (D antigen units) | 1-20 DU | 5 DU |
|  | MEF-1 Type 2 (D antigen units) | 1-20 DU | 2 DU |
|  | Saukett Type 3 (D antigen units) | 1-20 DU | 5 DU |
| 7 | Total Aluminium Content ($Al^{3+}$) | 0.1-1.2 mg | Preferably NMT 0.3 or NMT 0.55 or NMT 0.9 |
| 8 | 2-Phenoxyethanol | 1-6 mg | Preferably one of 2 or 2.5 or 3.25 mg |
| 9 | L-Histidine | 0.1-5 mg | Preferably one of 0.7 or 1 or 1.55 mg |

NMT—Not more than

In twentieth embodiment of the present disclosure, the combination vaccine composition/formulation comprising Dose reduced IPV is an all liquid hexavalent vaccine formulation comprising of:

TABLE 7

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 1-50 Lf | Preferably one of 10 or 22.5 or 25 Lf |
| 2 | Tetanus toxoid (T) | 1-30 Lf | Preferably one of 2 or 7.5 or 10 Lf |
| 3 | Inactivated *B. pertussis* antigen (wP) | 1-50 IOU | Preferably one of 12 or 15 or 16 IOU |
| 4 | HBs antigen | 1-20 µg | Preferably one of 8 or 10 or 12.5 µg |
| 5 | Hib PRP-TT conjugate antigen | 1-20 µg of PRP | Preferably one of 8 or 10 or 13 µg of PRP |
| 6 | Inactivated Polio Virus (IPV) Salk Serotype | | |
|  | Mahoney Type 1 (D antigen units) | 1-20 DU | 10 DU |
|  | MEF-1 Type 2 (D antigen units) | 1-20 DU | 2 DU |
|  | Saukett Type 3 (D antigen units) | 1-20 DU | 10 DU |
| 7 | Total Aluminium Content ($Al^{3+}$) | 0.1-1.2 mg | Preferably NMT 0.3 or NMT 0.55 or NMT 0.9 |
| 8 | 2-Phenoxyethanol | 1-6 mg | Preferably one of 2 or 2.5 or 3.25 mg |
| 9 | L-Histidine | 0.1-5 mg | Preferably one of 0.7 or 1 or 1.55 mg |

NMT—Not more than

In twenty first embodiment of the present disclosure, the combination vaccine composition/formulation comprising Dose reduced IPV is an all liquid hexavalent vaccine formulation comprising of:

TABLE 8

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 1-50 Lf | Preferably one of 10 or 22.5 or 25 Lf |
| 2 | Tetanus toxoid (T) | 1-30 Lf | Preferably one of 2 or 7.5 or 10 Lf |
| 3 | Inactivated *B. pertussis* antigen (wP) | 1-50 IOU | Preferably one of 12 or 15 or 16 IOU |
| 4 | HBs antigen | 1-20 µg | Preferably one of 8 or 10 or 12.5 µg |
| 5 | Hib PRP-TT conjugate antigen | 1-20 µg of PRP | Preferably one of 8 or 10 or 13 µg of PRP |
| 6 | Inactivated Polio Virus (IPV) Salk Serotype | | |
| | Mahoney Type 1 (D antigen units) | 1-20 DU | 10 DU |
| | MEF-1 Type 2 (D antigen units) | 1-20 DU | 2 DU |
| | Saukett Type 3 (D antigen units) | 1-20 DU | 5 DU |
| 7 | Total Aluminium Content ($Al^{3+}$) | 0.1-1.2 mg | Preferably NMT 0.3 or NMT 0.55 or NMT 0.9 |
| 8 | 2-Phenoxyethanol | 1-6 mg | Preferably one of 2 or 2.5 or 3.25 mg |
| 9 | L-Histidine | 0.1-5 mg | Preferably one of 0.7 or 1 or 1.55 mg |

NMT—Not more than

In twenty first embodiment of the present disclosure, the combination vaccine composition/formulation comprising Dose reduced IPV is an all liquid hexavalent vaccine formulation comprising of:

TABLE 9

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 1-50 Lf | Preferably one of 10 or 22.5 or 25 Lf |
| 2 | Tetanus toxoid (T) | 1-30 Lf | Preferably one of 2 or 7.5 or 10 Lf |
| 3 | Inactivated *B. pertussis* antigen (wP) | 1-50 IOU | Preferably one of 12 or 15 or 16 IOU |
| 4 | HBs antigen | 1-20 µg | Preferably one of 8 or 10 or 12.5 µg |
| 5 | Hib PRP-TT conjugate antigen | 1-20 µg of PRP | Preferably one of 8 or 10 or 13 µg of PRP |
| 6 | Inactivated Polio Virus (IPV) Salk Serotype | | |
| | Mahoney Type 1 (D antigen units) | 1-20 DU | 10 DU |
| | MEF-1 Type 2 (D antigen units) | 1-20 DU | 2 DU |
| | Saukett Type 3 (D antigen units) | 1-20 DU | 12 DU |
| 7 | Total Aluminium Content ($Al^{3+}$) | 0.1-1.2 mg | Preferably NMT 0.3 or NMT 0.55 or NMT 0.9 |
| 8 | 2-Phenoxyethanol | 1-6 mg | Preferably one of 2 or 2.5 or 3.25 mg |
| 9 | L-Histidine | 0.1-5 mg | Preferably one of 0.7 or 1 or 1.55 mg |

NMT—Not more than

In twenty second embodiment of the present disclosure, the combination vaccine composition/formulation comprising Dose reduced IPV is an all liquid hexavalent vaccine formulation comprising of:

TABLE 10

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 1-50 Lf | Preferably one of 10 or 22.5 or 25 Lf |
| 2 | Tetanus toxoid (T) | 1-30 Lf | Preferably one of 2 or 7.5 or 10 Lf |
| 3 | Inactivated *B. pertussis* antigen (wP) | 1-50 IOU | Preferably one of 12 or 15 or 16 IOU |
| 4 | HBs antigen | 1-20 µg | Preferably one of 8 or 10 or 12.5 µg |
| 5 | Hib PRP-TT conjugate antigen | 1-20 µg of PRP | Preferably one of 8 or 10 or 13 µg of PRP |

TABLE 10-continued

| Sr. No. | Formulation Components | Antigen Unit/0.5 ml Dose | Preferred Antigen Unit/0.5 ml Dose (In any of the combination) |
|---|---|---|---|
| 6 | Inactivated Polio Virus (IPV) Salk Serotype | | |
| | Mahoney Type 1 (D antigen units) | 1-20 DU | 10 DU |
| | MEF-1 Type 2 (D antigen units) | 1-20 DU | 2 DU |
| | Saukett Type 3 (D antigen units) | 1-20 DU | 16 DU |
| 7 | Total Aluminium Content ($Al^{3+}$) | 0.1-1.2 mg | Preferably NMT 0.3 or NMT 0.55 or NMT 0.9 |
| 8 | 2-Phenoxyethanol | 1-6 mg | Preferably one of 2 or 2.5 or 3.25 mg |
| 9 | L-Histidine | 0.1-5 mg | Preferably one of 0.7 or 1 or 1.55 mg |

NMT—Not more than

In twenty third embodiment of the present disclosure, one or more antigens of the final combination vaccine composition/formulation comprising Dose reduced IPV may not be substantially adsorbed on to any adjuvant.

In twenty fourth embodiment of the present disclosure, the pH of the composition/formulation may be in the range of pH 6.0 to pH 8.0; more preferably in the range of pH 6.0 to pH 7.5; still more preferably in the range of pH 6.2 to pH 7.2; and most preferably in the range of pH 6.3 to pH 6.8.

In twenty fifth embodiment of the present disclosure, WFI or 0.9% saline (NaCl) may be added to the final combination vaccine composition to make up the volume.

In twenty sixth embodiment of the present disclosure, the composition/formulation may additionally comprise of a buffering agent selected from the group consisting of carbonate, phosphate, acetate, succinate, borate, citrate, lactate, gluconate and tartrate, as well as more complex organic buffering agents including a phosphate buffering agent that contains sodium phosphate and/or potassium phosphate in a ratio selected to achieve the desired pH. In another example, the buffering agent contains Tris (hydroxymethyl) aminomethane, or "Tris", formulated to achieve the desired pH. Yet in another example, the buffering agent could be the minimum essential medium with Hanks salts. Other buffers, such as HEPES, piperazine-N,N'-bis (PIPES), and 2-ethanesulfonic acid (MES) are also envisaged by the present disclosure. The buffer aids in stabilizing the immunogenic composition of the present disclosure. The amount of the buffer may be in the range of 0.1 mM to 100 mM, preferably selected from 5 mM, 6 mM, 7 mM, 22 mM, 23 mM, 24 mM, 25 mM, 26 mM, 27 mM, 28 mM, 29 mM and 30 mM.

Yet another aspect of the embodiment, the composition/formulation may additionally comprise of pharmaceutically acceptable excipients selected from the group consisting of surfactants, polymers and salts. Examples of Surfactants may include non-ionic surfactants such as polysorbate 20, polysorbate 80, etc. Examples of the polymers may include dextran, carboxymethyl cellulose, hyaluronic acid, cyclodextrin, etc. Examples of the salts may include NaCl, KCl, $KH_2PO_4$, $Na_2HPO_4 \cdot 2H_2O$, $CaCl_2$, $MgCl_2$, etc. Preferably, the salt may be NaCl. Typically the amount of the salt may be in the range of 100 mM to 200 mM.

Amino acids, such as Histidine, glycine, arginine and lysine may be added to stabilize the immunogenic composition.

In twenty seventh embodiment of the present disclosure, the composition/formulation may additionally comprise of one or more adjuvant selected from the group of aluminium salt (Al3+) such as aluminium hydroxide ($Al(OH)_3$) or aluminium phosphate ($AlPO_4$), alum, calcium phosphate, MPLA, 3D-MPL, QS21, a CpG-containing oligodeoxynucleotide adjuvant, liposome, or oil-in-water emulsion.

Yet preferably the composition comprises aluminium phosphate ($AlPO_4$) as adjuvant.

Yet preferably the composition comprises aluminium hydroxide (AlOH3) as adjuvant.

In one of the aspects of the twenty seventh embodiment, antigens of the final formulation may be adsorbed on to in situ aluminium phosphate gel or readymade Aluminium phosphate gel or a combination thereof.

In one of the preferred aspects of the twenty seventh embodiment, the composition of the present disclosure may contain the adjuvant in an amount of 2.5 mg/0.5 ml or less, and specifically, in an amount of 1.5 mg/0.5 ml to 0.1 mg/0.5 ml.

In twenty eighth embodiment of the present disclosure, the composition may additionally comprise of an immunostimulatory component selected from the group consisting of an oil and water emulsion, MF-59, a liposome, a lipopolysaccharide, a saponin, lipid A, lipid A derivatives, Monophosphoryl lipid A, 3-deacylated monophosphoryl lipid A, AS01, AS03, an oligonucleotide, an oligonucleotide comprising at least one unmethylated CpG and/or a liposome, Freund's adjuvant, Freund's complete adjuvant, Freund's incomplete adjuvant, polymers, co-polymers such as polyoxyethylene-polyoxypropylene copolymers, including block co-polymers, polymer p 1005, CRL-8300 adjuvant, muramyl dipeptide, TLR-4 agonists, flagellin, flagellins derived from gram negative bacteria, TLR-5 agonists, fragments of flagellins capable of binding to TLR-5 receptors, Alpha-C-galactosylceramide, Chitosan, Interleukin-2, QS-21, ISCOMS, squalene mixtures (SAF-1), Quil A, cholera toxin B subunit, polyphosphazene and derivatives, *mycobacterium* cell wall preparations, mycolic acid derivatives, non-ionic block copolymer surfactants, OMV, fHbp, saponin combination with sterols and lipids.

In twenty ninth embodiment of the present disclosure, the composition may additionally comprise of preservative selected from the group consisting of methylparaben, propylparaben, Benzethonium chloride (Phemerol), Phenol, m-cresol, Thiomersal, Formaldehyde, benzalkonium chloride, benzyl alcohol, chlorobutanol, p-chlor-m-cresol, or benzyl alcohol or a combination thereof. A vaccine composition may include preservative for a single immunization, or may include preservative for multiple immunizations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material. Typically the amount of the preservative may be in the range of 0.1 mg to 50 mg.

Yet according to a preferred aspect of the twenty ninth embodiment, the composition may alternatively comprise of preservative combination selected from:
  i. 2-Phenoxyethanol in an amount of 1 to 6 mg per 0.5 ml (v/v); more preferably one of 2 or 2.5 or 3.25 mg per 0.5 ml (v/v) and methylparaben in an amount of 0.1-1.5 mg per 0.5 ml (w/v); more preferably one of 0.7 or 0.9 or 1 mg per 0.5 ml (w/v) or
  ii. 2-Phenoxyethanol in an amount of 1 to 6 mg per 0.5 ml (v/v); more preferably one of 2 or 2.5 or 3.25 mg per 0.5 ml (v/v) and propylparaben in an amount of 0.05-0.2 mg per 0.5 ml (w/v); more preferably one of 0.05 or 0.1 or 0.15 mg per 0.5 ml (w/v) or
  iii. 2-Phenoxyethanol in an amount of 1 to 6 mg per 0.5 ml (v/v); more preferably one of 2 or 2.5 or 3.25 mg per 0.5 ml (v/v), methylparaben in an amount of 0.1-1.5 mg per 0.5 ml (w/v); more preferably one of 0.7 or 0.9 or 1 mg per 0.5 ml (w/v) and propylparaben in an amount of 0.05-0.2 mg per 0.5 ml (w/v); more preferably one of 0.05 or 0.1 or 0.15 mg per 0.5 ml (w/v).

In thirtieth embodiment of the present disclosure, the composition may additionally comprise of auxiliary substances such as wetting or emulsifying agents, pH buffering agents, gelling or viscosity enhancing additives, flavoring agents, colors, and the like, depending upon the route of administration and the preparation desired.

In thirty first embodiment of the present disclosure, the composition may be fully liquid but is not limited thereto. Suitable forms of liquid preparation may include solutions, suspensions, emulsions, syrups, isotonic aqueous solutions, viscous compositions and elixirs that are buffered to a desired pH.

The composition of the present disclosure may be in the form of transdermal preparations including lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size. When in the form of solutions, suspensions and gels, in some embodiments, the immunogenic compositions contain a major amount of water (preferably purified water) in addition to the active ingredient(s).

In thirty second embodiment of the present disclosure, the said vaccine composition may be stable at 2-8 deg C. for 12 to 36 months; at 25 deg C. for 2 to 6 months; at 37 deg C. for 1 week to 4 weeks.

In thirty third embodiment of the present disclosure, the composition may be formulated for use in a method for reducing the onset of or preventing a health condition comprising diphtheria, tetanus, pertussis, hepatitis B virus, *Haemophilus influenzae* type b, polio virus infection involving administration of an immunologically effective amount of the immunogenic composition to a human subject via parenteral or subcutaneous or intradermal, intramuscular or intraperitoneal or intravenous administration or injectable administration or sustained release from implants or administration by eye drops or nasal or rectal or buccal or vaginal, peroral or intragastric or mucosal or perlinqual, alveolar or gingival or olfactory or respiratory mucosa administration or any other routes of immunization.

In thirty fourth embodiment of the present disclosure, the composition could be formulated as single dose vials or multidose vials (2 Dose or 5 Dose or 10 Dosevials) or multidose kit or as pre-filled syringes wherein the said immunogenic composition may be given in a single dose schedule, or preferably a multiple dose schedule in which a primary course of vaccination is followed by 1-3 separate doses given at subsequent time intervals after 1-3 years if needed. The dosage regimen will also, at least in part, be determined on the need of a booster dose required to confer protective immunity.

Yet preferably the composition may be formulated for administration to a human subject or children 2 years of age or below according to a two dose regimens consisting of a first dose, and second dose at subsequent time intervals after 1-3 years.

Yet preferably the composition may be administered concomitantly with other drugs or any other vaccine.

Compositions may be presented in vials, or they may be presented in ready filled syringes. The syringes may be supplied with or without needles. A syringe will include a single dose of the composition, whereas a vial may include a single dose or multiple doses (e.g. 2 doses). In one embodiment the dose is for human. In a further embodiment the dose is for an adult, adolescent, toddler, infant or less than one year old human and may be administered by injection.

Vaccines of the invention may be packaged in unit dose form or in multiple dose form (e.g. 2 doses). The said multidose composition can be selected from a group consisting of 2 dose, 5 dose and 10 dose. For multiple dose forms, vials are preferred to pre-filled syringes. Effective dosage volumes can be routinely established, but a typical human dose of the composition for injection has a volume of 0.5 mL.

Biological Source of Strains Used in Combination Vaccine:

Diphtheria Toxoid:

The strain *Corynebacterium diphtheriae* PW8 CN2000 was obtained from the Wellcome Research Laboratory, London, United Kingdom by the National Control Authority Central Research Institute (C.R.I.) Kasauli, Himachal Pradesh, India in lyophilized form in the year 1973. The strain was revived and further lyophilized under Master Seed Lot—*C. diphtheriae* CN2000 A1 at C.R.I. Kasauli.

Tetanus Toxoid:

The strain *Clostridium tetani* Harvard Strain No. 49205 was obtained from The Rijks Institute Voor de Volksgezondheid (Netherlands) by the National Control Authority C.R.I. Kasauli, in Lyophilized form.

Pertussis:

Manufacturing of Pertussis vaccine bulk at SIIPL involves usage of four strains of *Bordetella pertussis* viz. Strains 134, 509, 6229 and 25525. The Master Seed of Strains 134 and 509 are originally from Rijks Institute, The Netherlands, obtained through National Control Authority, Central Research Institute, Kasauli, Himachal Pradesh, India. The Master Seed of Strains 6229 and 25525 are originally from Lister Institute, England.

Hepatitis B:

Rhein Biotech (Germany) constructed the recombinant Hansenulapolymorpha strain containing the HBsAg surface antigen gene. Rhein Biotech also made the Master Cell Bank (MCB Hansenulapolymorpha K3/8-1 strain ADW, 12/94) and performed all the characterization tests on this bank.

*Haemophilus Influenzae* Type b:

The source organism for generation of cell substrate is *Haemophilus influenzae* type b, strain 760705. The strain was originally isolated from a 2 year and 2 months old baby boy (born on 14-8-74) in November 1976. Three passages of the strain took place before storage at −70° C. at the Academic Medical Centre (AMC), University of Amsterdam. This strain was transferred to SIIPL as a part of collaboration between SIIPL and Netherlands Vaccines Institute (NVI, The Netherlands).

IPV:
The strain and source of Salk poliovirus is given below.
Poliovirus Type 1:
Salk
Strain: Mahoney
Source: Bilthoven Biologicals, Netherlands
Sabin
Source: PT Bio Farma, Indonesia
Poliovirus Type 2:
Salk
Strain: MEF1
Source: Bilthoven Biologicals, Netherlands
Sabin
Source: PT Bio Farma, Indonesia
Poliovirus Type 3:
Salk
Strain: Saukett
Source: Bilthoven Biologicals, Netherlands
Sabin
Source: PT Bio Farma, Indonesia Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results. While certain embodiments of the inventions have been described, these embodiments have been presented by way of example only, and are not intended to limit the scope of the inventions. Variations or modifications to the formulation of this invention, within the scope of the invention, may occur to those skilled in the art upon reviewing the disclosure herein. Such variations or modifications are well within the spirit of this invention.

The numerical values given for various physical parameters, dimensions and quantities are only approximate values and it is envisaged that the values higher than the numerical value assigned to the physical parameters, dimensions and quantities fall within the scope of the invention unless there is a statement in the specification to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

EXAMPLES

The following examples are included to demonstrate preferred embodiments of the invention. It should be appreciated by those of skill in the art that the compositions and techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Purification of Sabin IPV (sIPV)

1. Tangential Flow Filtration (TFF):
Clarified harvest pool was concentrated to 10× using tangential flow filtration system with 100 Kda cassettes (0.5 m$^2$) and then diafiltered 3 times of harvest volume with phosphate buffer (30 mM-70 mM, pH: 7.0)

2. Column Chromatography: Ion Exchange Chromatography (IEC).
10×TFF concentrate was passed through DEAE Sepharose fast flow (Weak-Anion exchanger) packed in column xk-26 using Akta explorer (GE Healthcare). Negatively charged impurities was found to bind to the column whereas polio virus was collected in flow through with phosphate buffer (30 mM-70 mM, pH: 7.0)

3. Non-Phosphate Buffer (TRIS, TBS, MOPS, HEPES, and Bicarbonate) Exchange:
To minimize the loss of antigen in a quite cumbersome inactivation procedure (13 days), purified virus pool was buffer exchanged from phosphate buffer to Non-Phosphate Buffer (TRIS, TBS, MOPS, HEPES, and bicarbonate) (30 mM-70 mM, pH: 7) with TFF system (100 KDa, 0.1 m2). The purified virus pool was exchanged with three volumes of Non-Phosphate Buffer (TRIS, TBS, MOPS, HEPES, and bicarbonate).

Example 2—Inactivation of sIPV in Presence of Non-Phosphate Buffers (TRIS, TBS, MOPS, HEPES, and Bicarbonate) and Phosphate Buffer 10× concentrate diluted 10 times with M-199 (with 0.5% glycine) so as to achieve final concentration 1×. Inactivation agent formalin (0.025%) was added into purified virus bulk while constant mixing. Inactivation was carried out at 37° C. while continuous stirring for 13 days containing 0.22μ filtration on 7th day and 13th day.

TABLE 11

M-199 composition

| Component | Concentration (g/L) |
|---|---|
| Calcium Chloride | 0.2 |
| Ferric Nitrate•9H$_2$O | 0.00072 |
| Magnesium Sulfate (anhydrous) | 0.09767 |
| Potassium Chloride | 0.4 |
| Sodium Acetate (anhydrous) | 0.05 |
| Sodium Chloride | 6.8 |
| Sodium Phosphate Monobasic (anhydrous) | 0.122 |
| L-Alanine | 0.025 |
| L-Arginine•HCl | 0.07 |
| L-Aspartic Acid | 0.03 |
| L-Cysteine•HCl•H$_2$O | 0.00011 |
| L-Cystine•2HCl | 0.026 |
| L-Glutamic Acid | 0.0668 |
| L-Glutamine | 0.1 |
| Glycine | 0.05 |
| L-Histidine•HCl•H$_2$O | 0.02188 |
| Hydroxy-L-Proline | 0.01 |
| L-Isoleucine | 0.02 |
| L-Leucine | 0.06 |
| L-Lysine•HCl | 0.07 |

TABLE 11-continued

M-199 composition

| Component | Concentration (g/L) |
|---|---|
| L-Methionine | 0.015 |
| L-Phenylalanine | 0.025 |
| L-Proline | 0.04 |
| L-Serine | 0.025 |
| L-Threonine | 0.03 |
| L-Tryptophan | 0.01 |
| L-Tyrosine•2Na•2H$_2$O | 0.05766 |
| L-Valine | 0.025 |
| Ascorbic Acid•Na | 0.0000566 |
| D-Biotin | 0.00001 |
| Calciferol | 0.0001 |
| Choline Chloride | 0.0005 |
| Folic Acid | 0.00001 |
| Menadione (sodium bisulfite) | 0.000016 |
| myo-Inositol | 0.00005 |
| Niacinamide | 0.000025 |
| Nicotinic Acid | 0.000025 |
| p-Aminobenzoic Acid | 0.00005 |
| D-Pantothenic Acid (hemicalcium) | 0.00001 |
| Pyridoxal•HCl | 0.000025 |
| Pyridoxine•HCl | 0.000025 |
| Retinol Acetate | 0.00014 |
| Riboflavin | 0.00001 |
| DL-α-Tocopherol Phosphate•Na | 0.00001 |
| Thiamine•HCl | 0.00001 |
| Adenine Sulfate | 0.01 |
| Adenosine Triphosphate•2Na | 0.001 |
| Adenosine Monophosphate•Na | 0.0002385 |
| Cholesterol | 0.0002 |
| Deoxyribose | 0.0005 |
| Glucose | 1 |
| Glutathione (reduced) | 0.00005 |
| Guanine•HCl | 0.0003 |
| Hypoxanthine | 0.0003 |
| Phenol Red•Na | 0.0213 |
| Polyoxyethylenesorbitan Monooleate (TWEEN 80) | 0.02 |
| Ribose | 0.0005 |
| Thymine | 0.0003 |
| Uracil | 0.0003 |
| Xanthine•Na | 0.000344 |
| Sodium Bicarbonate | 2.2 |

A. Effect of Non-Phosphate Buffers (TRIS) on D Antigen Loss Compared to Phosphate Buffer:

TABLE 12

D-Antigen Units (DU/ml) before Formalin inactivation and after Formalin inactivation in presence of TRIS buffer (30 mM at pH 7.0)

| | IPV 1 | IPV 2 | IPV 3 |
|---|---|---|---|
| Before Formalin inactivation | 607.3 | 193.9 | 40.7 |
| After Formalin inactivation | 408.1 | 181.4 | 34.1 |

TABLE 13

D-Antigen Units (DU/ml) before Formalin inactivation and after Formalin inactivation in presence of TRIS (40 mM at pH 7.0)

| | IPV 1 | IPV 2 | IPV 3 |
|---|---|---|---|
| Before Formalin inactivation | 607.3 | 193.9 | 40.7 |
| After Formalin inactivation | 487.1 | 185.2 | 37.9 |

TABLE 14

D-Antigen Units (DU/ml) before Formalin inactivation and after Formalin inactivation in presence of TRIS buffer (50 mM at pH 7.0)

| | IPV 1 | IPV 2 | IPV 3 |
|---|---|---|---|
| Before Formalin inactivation | 607.3 | 193.9 | 40.7 |
| After Formalin inactivation | 451.9 | 175.9 | 31.0 |

When formaldehyde inactivation methods were particularly carried out in presence of phosphate buffer, significant D-antigen losses were observed, whereas it was found that formaldehyde inactivation in presence of Non-Phosphate Buffer (TRIS) resulted in minimum loss of D-antigen. Further, TRIS Buffer at a concentration of 40 mM was found to be most efficient in terms of D-Antigen content preservation for sIPV 1, 2 and 3.

B. Effect of Non-Phosphate Buffers Other than TRIS (TBS, MOPS, HEPES, and Bicarbonate) on D Antigen Loss Compared to Phosphate Buffer:

TABLE 15

D-Antigen Units (DU/ml) before Formalin inactivation and after Formalin inactivation in presence of phosphate buffer (40 mM at pH 7.0)

| | IPV 1 | IPV 2 | IPV 3 |
|---|---|---|---|
| Before Formalin inactivation | 607.3 | 193.9 | 40.7 |
| After Formalin inactivation | 52.7 | 22.63 | 4.21 |

TABLE 16

D-Antigen Units (DU/ml) before Formalin inactivation and after Formalin inactivation in presence of TBS (40 mM at pH 7.0)

| | IPV 1 | IPV 2 | IPV 3 |
|---|---|---|---|
| Before Formalin inactivation | 607.3 | 193.9 | 40.7 |
| After Formalin inactivation | 399.15 | 170.5 | 22 |

TABLE 17

D-Antigen Units (DU/ml) before Formalin inactivation and after Formalin inactivation in presence of MOPS (40 mM at pH 7.0)

| | IPV 1 | IPV 2 | IPV 3 |
|---|---|---|---|
| Before Formalin inactivation | 607.3 | 193.9 | 40.7 |
| After Formalin inactivation | 400.21 | 165 | 20.1 |

TABLE 18

D-Antigen Units (DU/ml) before Formalin inactivation and after Formalin inactivation in presence of HEPES (40 mM at pH 7.0)

| | IPV 1 | IPV 2 | IPV 3 |
|---|---|---|---|
| Before Formalin inactivation | 607.3 | 193.9 | 40.7 |
| After Formalin inactivation | 385.45 | 172 | 19.9 |

TABLE 19

D-Antigen Units (DU/ml) before Formalin inactivation and after Formalin inactivation in presence of bicarbonate (40 mM at pH 7.0)

|  | IPV 1 | IPV 2 | IPV 3 |
|---|---|---|---|
| Before Formalin inactivation | 607.3 | 193.9 | 40.7 |
| After Formalin inactivation | 395.6 | 179 | 21.3 |

When formaldehyde inactivation methods were particularly carried out in presence of phosphate buffer, significant D-antigen losses were observed, whereas it was found that formaldehyde inactivation in presence of Non-Phosphate Buffer other than TRIS (TBS, MOPS, HEPES, and bicarbonate) resulted in minimum loss of D-antigen.

Method: D-Antigen Content Determination by ELISA.

Day 1: Plate Coating:
1. 100 µl of specific bovine anti polio was pipetted in PBS per well
2. Microtiter plate was sealed and incubated overnight at room temperature.

Day 2: Blocking:
1. The plates were washed (Washing/dilution buffer –0.05% tween 20 in 1×PBS)3 times.
2. 300 µl block buffer (1% BSA in PBS) was pipetted per well.
3. The plate was sealed and incubated for 45 minutes at 37±1° C.

Sample Addition:
1. The plate was washed 3 times.
2. 100 µl of sample diluent was added in all wells except well of row A.
3. 100 µl standard was added to first two wells of column 2 and 3.
4. 100 µl sample was added to first two wells of column 4-12.
5. Prediluting sample to a suitable concentration.
6. 100 µl sample diluents was added to first two wells of column 1.
7. Serial two fold dilution were made down the column by transferring 100 ul from each well to adjacent well of the same column and discarding 100 ul from the last well.
8. Incubating at 37° C. for 2 hr.
9. Plates were kept overnight at 4° C.

Day 3: Monoclonal Antibody Addition:
1. The plate was washed 3 times.
2. 100 µl diluted (1:240) type specific monoclonal antibodies were added.
3. The plates were sealed and incubated for 2 hours at 37° C.

Conjugate:
1. The plate were washed 3 times
2. 100 µl diluted conjugate (Type1—1:2400, Type2—1:1500, Type3—1:4800) was added.
3. The plate was sealed and incubated for 1 hour at 37° C.

Substrate Addition:
1. 100 µl TMB substrate was added to all wells.
2. Mixture incubated at room temperature for 10 minutes.
3. Reaction was stopped by adding 100 µl 2M H2SO4.
4. Plate was read at 450/630 nm.
5. D antigen concentration was calculated using KC4 software.

Example 3—Adsorption of sIPV

1. Autoclaved 1% stock of $Al(OH)_3$ and $AlPO_4$ was used for the preparation of formulations.
2. Desired volume of $Al(OH)_3/AlPO_4$ was taken to get the required concentration of alum in a 100 ml glass bottle.
3. Inactivated polio virus bulk with known D-Ag Unit was added and volume make up was done with diluent.
4. Final formulation pH was adjusted to 6.5 with 1 N HCl/NaOH
5. The formulation bulk was kept on magnetic stirrer overnight at 2-8° C.

Example 4—Preformulation Studies

Different concentrations of $Al(OH)_3$ & $AlPO_4$ were prepared in 0.9% saline and in WFI to check size and zeta potential with respect to change in pH.

Figure 2:
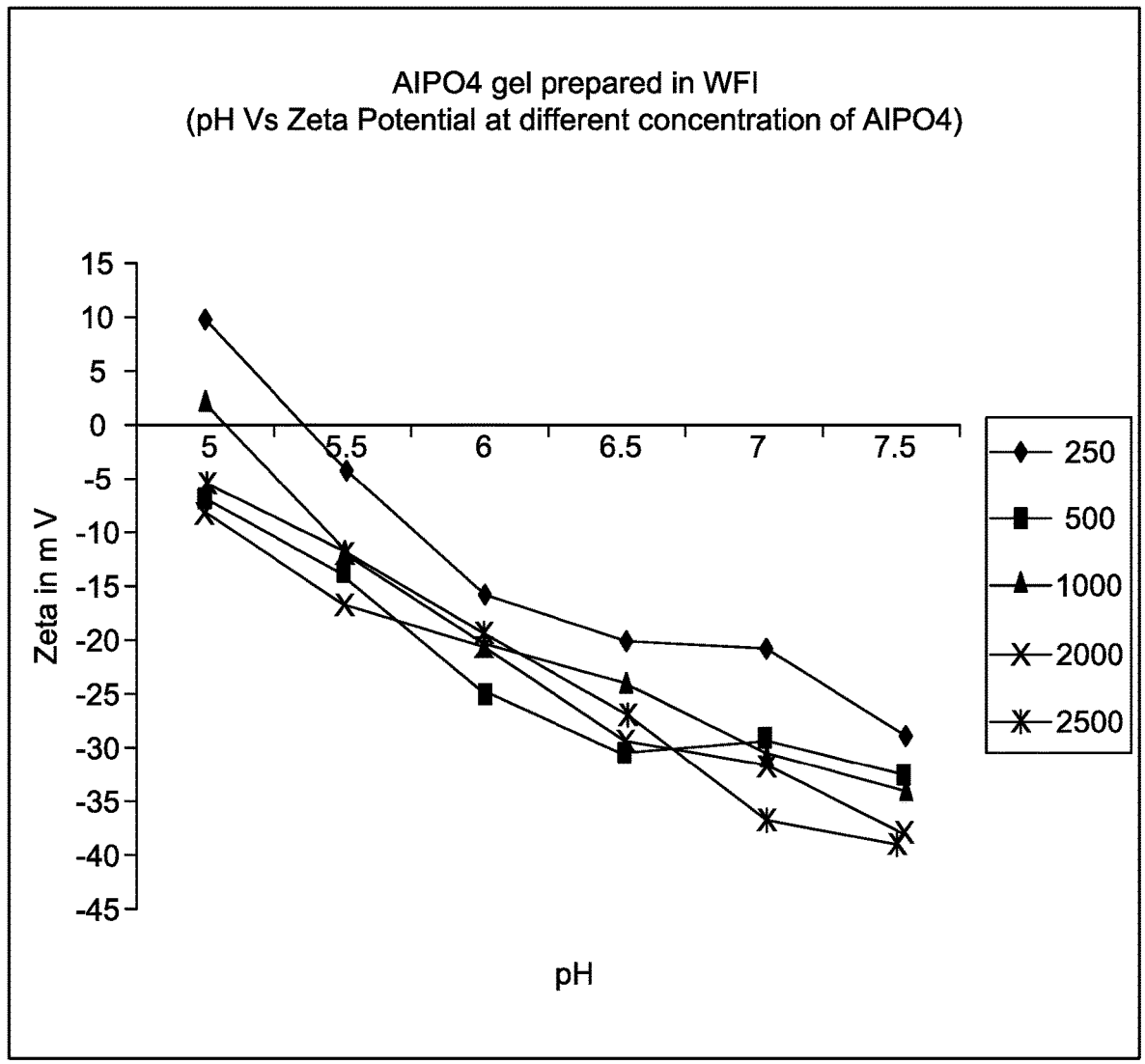
FIG. 2: Alum phosphate gel prepared in WFI (pH Vs Zeta potential at different concentrations of Alum phosphate gel).

It was observed that zeta potential of $AlPO_4$ decreases (negativity) with increase in pH from 5 to 7.5 in presence of WFI as well as in saline (Refer FIGS. 1 and 2).

Figure 3:
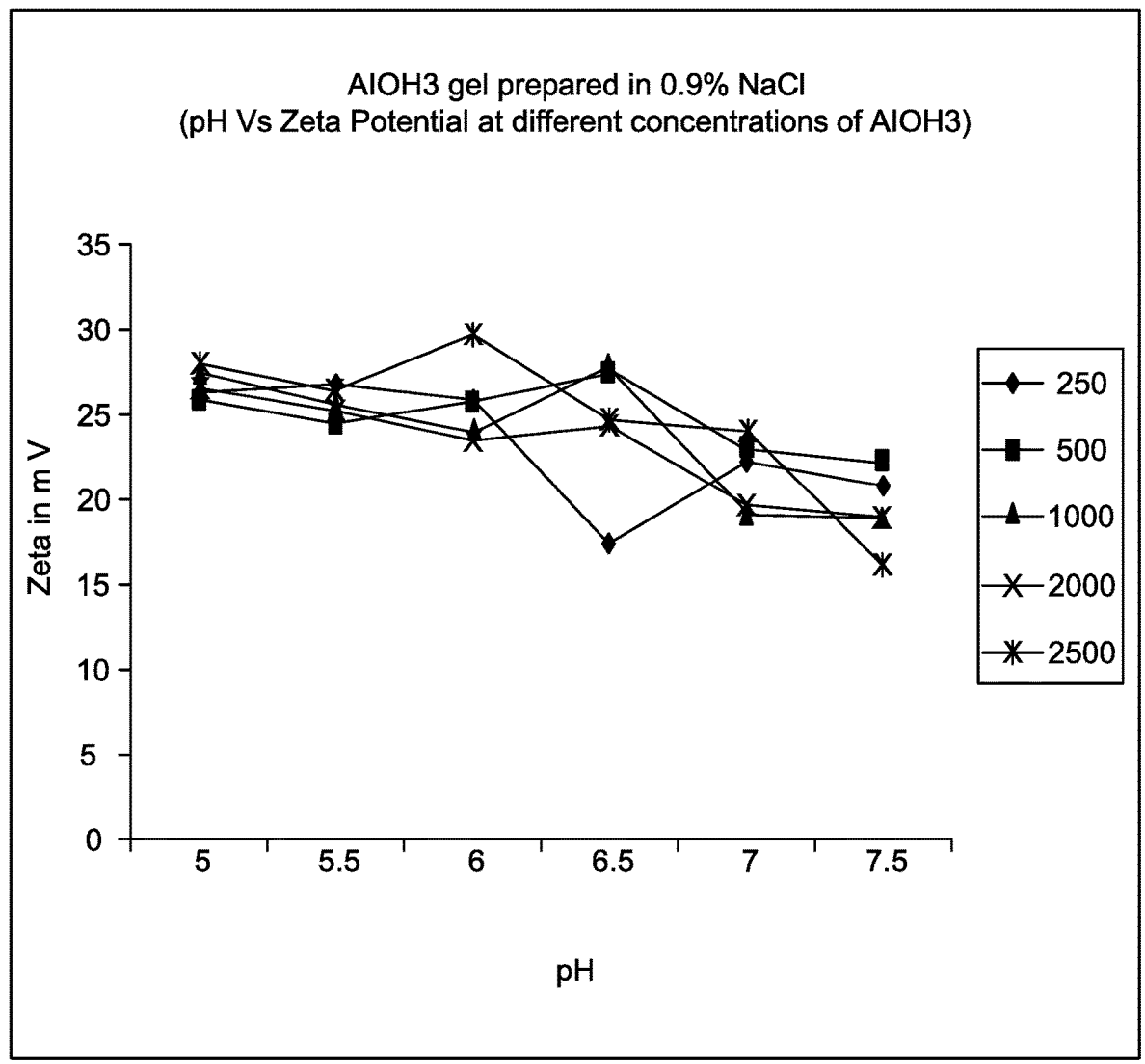
FIG. 3: Alum Hydroxide gel prepared in 0.9% NaCl (pH Vs Zeta potential at different concentrations of Alum hydroxide gel).
Figure 4:
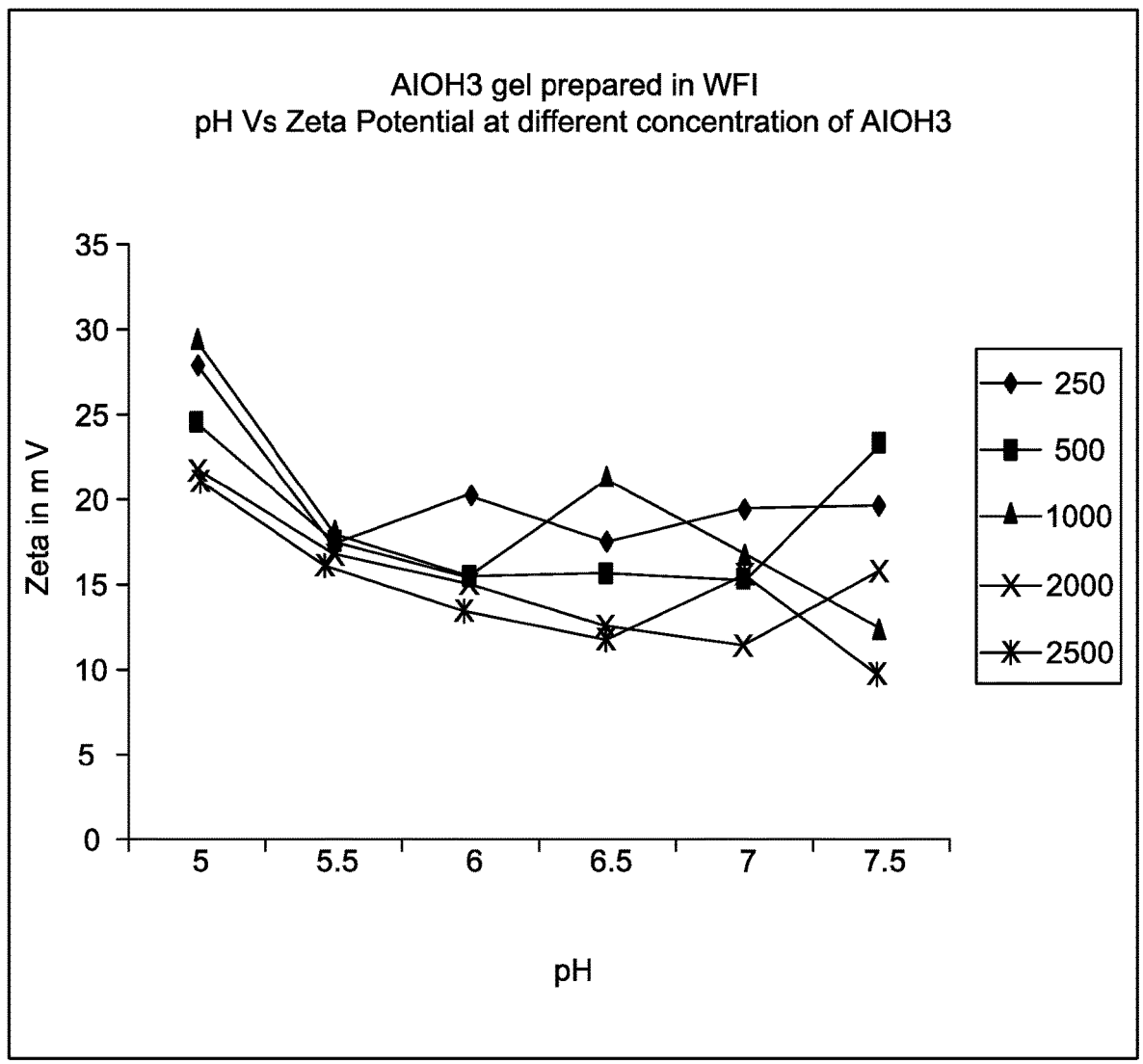
FIG. 4: Alum Hydroxide gel prepared in WFI (pH Vs Zeta potential at different concentrations of Alum hydroxide gel).

Whereas, zeta potential of $Al(OH)_3$ in saline remains constant, independent of pH and $Al(OH)_3$ salt concentration (Refer FIGS. 3 and 4).

Example 5—Adsorption Studies of sIPV on Alum Phosphate and Alum Hydroxide

TABLE 20

Sabin Type 1, 2 & 3 (Titer $10^{6.0}$/dose) adsorption on alum (Alum phosphate and Alum Hydroxide)

| Sample | | Titer (per does) | Virus Particles (in K) | % free in SUP | % adsorbed on gel |
|---|---|---|---|---|---|
| Type 1, $AlOH_3$ | Control | 5.45 | 284 | NA | |
| | Al+++ 125 ug/dose | 4.15 | 14 | 4.98 | 95.02 |
| | Al+++ 250 ug/dose | 3.85 | 7 | 2.49 | 97.51 |
| | Al+++ 500 ug/dose | 3.8 | 6.3 | 2.24 | 97.78 |
| Type 1, $AlPO_4$ | Control | 5.84 | 691 | NA | |
| | Al+++ 125 ug/dose | 3.49 | 3 | 0.43 | 99.57 |
| | Al+++ 250 ug/dose | 3.09 | 1.2 | 0.17 | 99.83 |
| | Al+++ 500 ug/dose | 2.94 | 0.87 | 0.12 | 99.87 |
| Type 2, $AlOH_3$ | Control | 5.49 | 309 | NA | |
| | Al+++ 125 ug/dose | 3.59 | 3.89 | 1.25 | 98.75 |
| | Al+++ 250 ug/dose | 3.49 | 3.09 | 1 | 99 |
| | Al+++ 500 ug/dose | 3.49 | 3.09 | 1 | 99 |
| Type 2, $AlPO_4$ | Control | 5.49 | 309 | NA | |
| | Al+++ 125 ug/dose | 3.15 | 1.41 | 0.45 | 99.5 |
| | Al+++ 250 ug/dose | 3.09 | 1.23 | 0.39 | 99.6 |
| | Al+++ 500 ug/dose | 3.09 | 1.23 | 0.39 | 99.6 |
| Type 3, $AlOH_3$ | Control | 5.59 | 389 | NA | |
| | Al+++ 125 ug/dose | 4.14 | 13.8 | 3.54 | 96.47 |
| | Al+++ 250 ug/dose | 3.94 | 8.7 | 2.23 | 97.77 |
| | Al+++ 500 ug/dose | 3.54 | 3.4 | 0.87 | 99.13 |

TABLE 20-continued

Sabin Type 1, 2 & 3 (Titer $10^{6.0}$/dose) adsorption on alum (Alum phosphate and Alum Hydroxide)

| | Sample | Titer (per does) | Virus Particles (in K) | % free in SUP | % adsorbed on gel |
|---|---|---|---|---|---|
| Type 3, AlPO$_4$ | Control | 5.59 | 389 | | NA |
| | Al+++ 125 ug/dose | 5.34 | 218 | 56.04 | 43.96 |
| | Al+++ 250 ug/dose | 5.24 | 173 | 44.47 | 55.53 |
| | Al+++ 500 ug/dose | 5.16 | 144 | 37.01 | 62.9 |

It was found that Sabin polio virus type-3 shows only 50-60% adsorption with aluminium phosphate (AlPO$_4$). Whereas, Sabin polio virus type-3 shows at least 90% adsorption with Al(OH)$_3$. Thus, Alum hydroxide was found to be more efficient as compared to Alum phosphate with respect to adsorption of Sabin Type 1, 2 and 3.

Example 6—Immunogenicity Studies of Alum Adsorbed sIPV

To check immune response of adjuvanted sIPV in rat (Sera Neutralization Test) SNT test was carried out. Sera was separated and used to test the presence of neutralizing antibodies for type specific polio virus. Control sera used to validate the test. Virus back-titration was also performed to get the number of challenge virus particles added.

Animal Model: Wistar rat (8 weeks, approx 200 gm) 50% male and 50% female per group.

Route of Inoculation: Intra Muscular.

Volume: 0.5 ml

Blood withdrawal: on day 21.

Site of bleeding: Retro-Orbital plexus.

Interpretation: It was surprisingly found that Alum hydroxide adjuvanted Type 1 Sabin IPV having 5 DU/dose gave better seroconversion as compared to Salk IPV vaccine with 40 DU/dose and Alum phosphate adjuvanted Sabin IPV having 5 DU/dose.

TABLE 22

| Immunogenicity results of Alum Adsorbed sIPV Type 2 | | | | | | |
|---|---|---|---|---|---|---|
| Rat | Group 1 4 DU(0.6 mgOH) | | Group 2 8 DU(0.6 mgOH) | | Group 3 16 DU 0.6 mgOH | |
| No | SNT +ve | Sera Titer | SNT +ve | Sera Titer | SNT +ve | Sera Titer |
| 1 | 3 | (1:8) | 4 | (1:16) | 7 | (1:128) |
| 2 | 4 | (1:16) | 6 | (1:64) | 5 | (1:32) |
| 3 | 0 | (<1:2) | 3 | (1:8) | 5 | (1:32) |
| 4 | 3 | (1:8) | 4 | (1:16) | 6 | (1:64) |
| 5 | 5 | (1:32) | 7 | (1:128) | 6 | (1:64) |
| 6 | 6 | (1:64) | 4 | (1:16) | 9 | (1:512) |
| 7 | 4 | (1:16) | 7 | (1:128) | 4 | (1:16) |
| 8 | 5 | (1:32) | 3 | (1:8) | 8 | (1:256) |
| 9 | 7 | (1:128) | 8 | (1:256) | 8 | (1:256) |
| 10 | 5 | (1:32) | 3 | (1:8) | 8 | (1:256) |

Interpretation: Type 2 sIPV having 8 DU/dose with adjuvant gave equivalent seroconversion as compared to Salk IPV vaccine with 8 DU/dose.

TABLE 23

| Immunogenicity results of Alum Adsorbed sIPV Type 3 | | | | | | |
|---|---|---|---|---|---|---|
| Rat | Group 1 10 DU 0.6mgOH | | Group 2 5 DU 0.6 mgOH | | Group 3 2.5 DU 0.6 mgOH | |
| No | SNT +ve | Sera Titer | SNT +ve | Sera Titer | SNT +ve | Sera Titer |
| 1 | 3 | (1:8) | 2 | (1:4) | 0 | (<1:2) |
| 2 | 0 | (<1:2) | 5 | (1:32) | 1 | (1:2) |
| 3 | 2 | (1:4) | 3 | (1:8) | 1 | (1:2) |
| 4 | 4 | (1:16) | 2 | (1:4) | 0 | (<1:2) |

TABLE 21

| Immunogenicity results of Alum Adsorbed sIPV Type 1 | | | | | | | | | | | | | | | | |
|---|---|---|---|---|---|---|---|---|---|---|---|---|---|---|---|---|
| | Group 1 Comm. IPV | | Group 2 5 DU 1.15 mgOH | | Group 3 2.5 DU 1.15 mgOH | | Group 4 1 DU 1.15 mgOH | | Group 5 5 DU 1.8 mgPO4 | | Group 6 2.5 DU 1.8 mgPO4 | | Group 7 1 DU 1.8 mgPO4 | | Group 15 −ve control | |
| Rat No. | SNT +ve | Sera Titer | SNT +ve | Sera Titer | SNT +ve | Sera Titer | SNT +ve | Sera Titer | SNT +ve | Sera Titer | SNT +ve | Sera Titer | SNT +ve | Sera Titer | SNT +ve | Sera Titer |
| 1 | 1 | (1:2) | 8 | (1:256) | 1 | (1:2) | 4 | (1:16) | 5 | (1:32) | 5 | (1:32) | 2 | (1:4) | 0 | (<1:2) |
| 2 | 1 | (1:2) | 5 | (1:32) | 1 | (1:2) | 7 | (1:128) | 8 | (1:256) | 4 | (1:16) | 1 | (1:2) | 0 | (<1:2) |
| 3 | 0 | (<1:2) | 7 | (1:128) | 3 | (1:8) | 0 | (<1.2) | 4 | (1:16) | 6 | (1:64) | 0 | (<1:2) | 0 | (<1:2) |
| 4 | 0 | (<1:2) | 11 | (1:2048) | 2 | (1:4) | 2 | (1:4) | 1 | (1:2) | 5 | (1:32) | 0 | (<1:2) | 0 | (<1:2) |
| 5 | 7 | (1:128) | 3 | (1:8) | 7 | (1:128) | 5 | (1:32) | 6 | (1:64) | 4 | (1:16) | 1 | (1:2) | 0 | (<1:2) |
| 6 | 4 | (1:16) | 7 | (1:128) | 7 | (1:128) | 1 | (1:2) | 5 | (1:32) | 6 | (1:64) | 3 | (1:8) | 0 | (<1:2) |
| 7 | 3 | (1:8) | 5 | (1:32) | 4 | (1:16) | 1 | (1:2) | 8 | (1:256) | 7 | (1:128) | 0 | (<1:2) | 0 | (<1:2) |
| 8 | 1 | (1:2) | 7 | (1:128) | 3 | (1:8) | 2 | (1:4) | 6 | (1:64) | 0 | (<1:2) | 0 | (<1:2) | 0 | (<1:2) |
| 9 | 3 | (1:8) | 8 | (1:356) | 2 | (1:4) | 3 | (1:8) | 8 | (1:256) | 4 | (1:16) | 4 | (1:16) | 0 | (<1:2) |
| 10 | 3 | (1:8) | 7 | (1:128) | 4 | (1:16) | 5 | (1:32) | 6 | (1:64) | 2 | (1:4) | 2 | (1:4) | 0 | (<1:2) |

TABLE 23-continued

Immunogenicity results of Alum Adsorbed sIPV Type 3

| Rat No | Group 1 10 DU 0.6mgOH | | Group 2 5 DU 0.6 mgOH | | Group 3 2.5 DU 0.6 mgOH | |
|---|---|---|---|---|---|---|
| | SNT +ve | Sera Titer | SNT +ve | Sera Titer | SNT +ve | Sera Titer |
| 5 | 4 | (1:16) | 2 | (1:4) | 1 | (1:2) |
| 6 | 4 | (1:16) | 1 | (1:2) | 1 | (1:2) |
| 7 | 9 | (1:512) | 0 | (<1:2) | 2 | (1:4) |
| 8 | 7 | (1:128) | 2 | (1:4) | 2 | (1:4) |
| 9 | 1 | (1:2) | 0 | (<1:2) | 1 | (1:2) |
| 10 | 5 | (1:32) | 7 | (1:128 | 1 | (1:2) |

Interpretation: It was found that Type 3 sIPV having 10 DU/dose with adjuvant gave equivalent sero conversion as compared to Salk IPV vaccine with 32 DU/dose.

TABLE 24

Maximum dose reduction observed for individual Sabin Type 1, 2 & 3 after studies

| sIPV | Standard dose | *SIIL Dose | Dose reduction |
|---|---|---|---|
| Type 1 | 40 DU | 5 DU | ~8 Folds |
| Type 2 | 8 DU | 8 DU | Equivalent |
| Type 3 | 32 DU | 10 DU | ~3 Folds |

*SIIL: Serum Institute of India In House dose reduced IPV preparation.

TABLE 25

Immune response study of the adjuvanted SABIN poliovirus

| | Type 1 | Type 2 | Type 3 |
|---|---|---|---|
| D-Antigen units of Sabin's strain | 5 | 16 | 10 |
| | 2.5 | 8 | 5 |
| | 7.5 | 16 | 10 |

Interpretation:

We observed that if the viruses are adjuvanted with Al(OH)$_3$ shows excellent dose sparing.

If we consider single dose regimen for immunization then 5-16-10 D-Ag are best combination for Sabin's polio type 1, 2 and 3 respectively.

If we consider two doses for immunization then 2.5-8-5 gives excellent immunity.

TABLE 26

Immune response study of the adjuvanted SALK poliovirus

| | Type 1 | Type 2 | Type 3 |
|---|---|---|---|
| D-antigen units for Salk Strain | 8 | 2 | 5 |
| | 5 | 2 | 5 |
| | 10 | 2 | 10 |
| | 7.5 | 16 | 10 |
| | 10 | 2 | 5 |
| | 10 | 2 | 12 |
| | 10 | 2 | 16 |

Interpretation:

We observed that if the viruses are adjuvanted with Al(OH)$_3$ shows excellent dose sparing.

If we consider single dose regimen for immunization then 8-2-5 D-Ag are best combination for Salk's polio type 1, 2 and 3 respectively.

If we consider two doses for immunization then 5-2-5 gives excellent immunity.

Example 7: Purification of Diphtheria Toxoid (D) and Tetanus Toxoid (T)

Tetanus Toxoid and Diphtheria toxoid was purified using Gel filtration chromatography and stabilized by addition of an amino acid buffer solution (Histidine, lysine, glycine, arginine) or polysorbate solution at a final concentration of 5-300 mM, and stored at temperature −20 to +40° C. till further use.

TABLE 27

Gel filtration chromatography Process Parameters

| Sr. No. | Parameter | Details |
|---|---|---|
| 1 | Method of Purification | Gel Filtration Chromatography (GFC) |
| 2 | Resin | Sephacryl S-300 HR |
| 3 | Column Used | XK 26/70 cm |
| 4 | Column Packed bed height | ~50 cm |
| 5 | Linear Flow rate | 1-3 ml/min |
| 6 | Sample (T) loading | 4% of total bed volume |
| 7 | Fraction Collection | 5 ml each (2 min) |
| 8 | Analysis | Lowry's assay, LF estimation, % Monomer |
| 8 | Buffer | 0.85% NaCl pH 6-7 |

Figure 5:
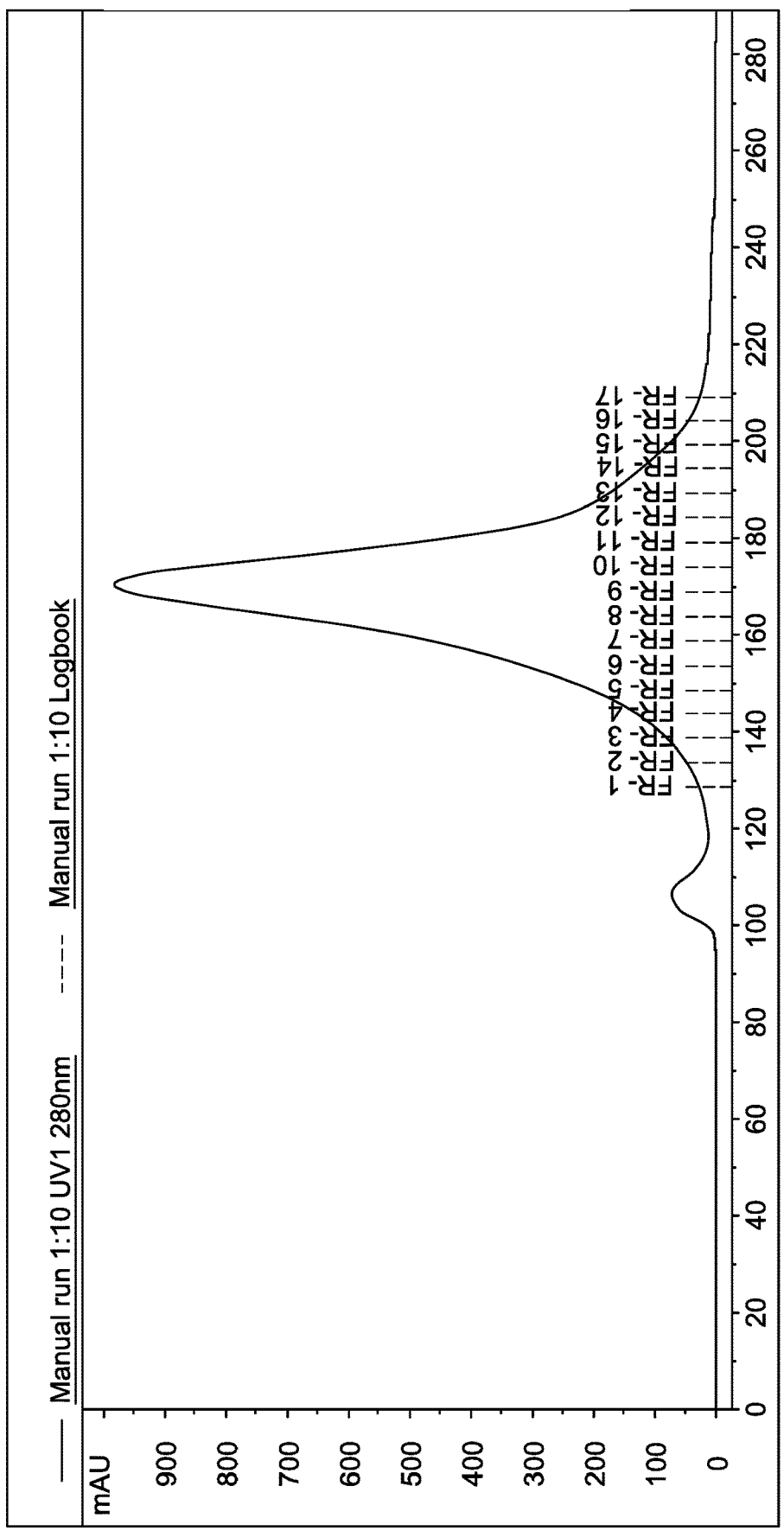
FIG. 5: Diphtheria Toxoid Purification—Chromatogram of Gel Filtration Chromatography Sephacryl S-300 HR, Column XK 26/70. X axis represents volume (ml) and Y axis represents UV at 280 nm (mAU).

Refer FIG. 5: Diphtheria Toxoid Purification - Chromatogram of Gel Filtration Chromatography

TABLE 28

% Recovery & Monomer content of purified Diphtheria toxoid

| No. | Sample | Protein Conc. (mg/mL) | % Monomer | % Recovery |
|---|---|---|---|---|
| 1 | Native DT | — | 67.19 | — |
| 2 | Native CRM | — | 86.96 | — |
| 3 | GFC DT FR 8 | 2.03 | 83.21 | Injected DT Qty |
| 4 | GFC DT FR 9 | 3.38 | 87.15 | 120 mg |
| 5 | GFC DT FR 10 | 4.08 | 87.24 | Obtained Qty |
| 6 | GFC DT FR 11 | 3.52 | 86.60 | 75.1 mg (62.5%) |
| 7 | GFC DT FR 12 | 2.01 | 89.97 | |
| 8 | GFC DT FR 10-11 | 3.83 | 86.03 | 31.6% |
| 9 | GFC DT FR 9-12 | 2.96 | 87.42 | 48.9% |
| 10 | GFC DT FR 7-13 | 2.19 | 86.24 | 63.3% |

Results:

The percent monomer content was found to be in the range of 80-90%.

Example 8: Preparation of Hib PRP—Protein Conjugate a) PRP Polysaccharide was Produced as Follows:

*H. Influenzae* type-b bacteria was grown in semi synthetic media under certain conditions of temperature, agitation and optical density etc. PRP is an outer membrane bound polysaccharide, gets released into the medium during the fermentation under agitation condition. Fermented biomass separated broth contains crude PRP, which is again purified by precipitation using a detergent N,N, N-trimethyl-1-hexadecanaminium bromide, followed by ethanol gradient precipitation and filtration. Final purified PRP polysaccharide was tested for meeting the specifications like endotoxin, nucleic acid and protein as per the WHO, BP, EP, IP etc.

b) Hib PRP-CRM$_{197}$ Carrier Protein Conjugate was Prepared as Follows:

The polysaccharide conjugate was prepared by coupling of PRP polysaccharide with a CRM$_{197}$ carrier protein. The input ratio of reactants i.e. PRP polysaccharide, CDAP and $CRM_{197}$ was selected at 1:1.5:1 ratio for conjugation reaction. During conjugation, purified PRP polysaccharide was depolymerized using an alkaline buffer (0.4M Carb-Bicarbonate buffer, pH 10.5±0.1) to achieve size reduced PRP. Size reduced PRP is treated for cyanylation using CDAP (1-cyano-4-dimethylamino pyridinium tetrafluoroborate) chemistry to form a cyanate ester. The activated cyanylated polysaccharide may thus be coupled directly with amino group on the carrier protein $CRM_{197}$. The degree of conversion of Hib conjugate was confirmed by the HPLC. The conjugation reaction was quenched by achieving the desired level of conversion of conjugate with the specification of not less than 65% conversion of Hib conjugate, and then conjugate reaction was neutralized by Glycine (2M) addition. The Hib PRP-$CRM_{197}$ Conjugate is purified on ultra-filtration membrane filters (300 kDa and 100 kDa) to remove nonreactive reagents and by-products. Final conjugate bulk was 0.22 μm filtered and stored at 2-8° C.

Quality Characteristics of Hib PRP-$CRM_{197}$ Conjugate Antigen Obtained were as Follow:

| | |
|---|---|
| PRP content (mg/mL): | 1.49 |
| Protein content (mg/mL): | 2.98 |
| Ratio (Ps:Protein): | 0.52 |
| Free PRP (%): | 1.77 |
| PMW (kD): | 983 |
| Avg MW (kD): | 752 | c) Hib PRP-TT Carrier Protein Conjugate was Prepared as Follows:

The concentrated polysaccharide is depolymerized under mild alkaline conditions using carbonate-bicarbonate buffer. After target polysaccharide size is reached, the depolymerized polysaccharide is activated using Cyanogen Bromide. This activation is done under nitrogen environment. Freshly prepared adipic acid dihydrazide (ADH) solution is added within 6-10 minutes to the reaction mixture obtained. The reaction is carried out for NLT 16 hours at 2-10° C. The reaction mixture obtained is concentrated and diafiltered volume by volume with phosphate buffer saline (PBS) using 10 kD NMWCO UF membrane to remove free ADH. The removal of ADH is monitored on HPLC and diafiltration is continued till free ADH level reaches below 5%. The resulting retentate is further diafiltered with NLT 5×MES-NaCl buffer. This is further concentrated to achieve a concentration of NLT 20 mg/mL. The retentate is passed through a 0.22 μm filter, which serves as a clarification step. The filtered activated polysaccharide is collected, sampled, aliquoted and stored at 2-8° C. till further processing. A sample is drawn from the processed polysaccharide pool for analysis, which includes PRP molecular size (kD), PRP content, and PRP degree of activation. The conjugation reaction requires two components viz. processed polysaccharide and the carrier protein (TT). The carrier protein is concentrated and diafiltered with MES-NaCl buffer using 10 kD UF NMWCO membrane. This diafiltered carrier-protein is then further concentrated to NLT 20 mg/mL using the same membrane. The two components are mixed in appropriate quantities in the ratio of PRP:TT=1:1 (w/w) in presence of EDC under stirring. The conjugation reaction is quenched using phosphate EDTA buffer. The conjugation reaction is monitored on HPLC and is continued till >85% conversion of protein (based on the free protein conversion to conjugate) is reached.

Quality Characteristics of Hib PRP-TT Conjugate Antigen Obtained were as Follow:

| | |
|---|---|
| PRP content (μg/0.5 ml): | 8.1 |
| Ratio (PRP:TT): | 0.5 |
| Free PRP (%): | 4.8% |
| PMW (kD): | 983 |
| Avg MW (kD): | 752 |

Example 9: Process of Manufacturing Inactivated wP Antigen

Inactivation Method of Whole Cell Pertussis (wP) Antigen:

Inactivation method optimization is done after performing various experiments which include inactivation at 56° C. for 10 min in presence of formaldehyde, 56° C. for 15 min in presence of formaldehyde, 56° C. for 10 min in presence of hymine, 56° C. for 15 min in presence of hymine and only heating at 56° C. for 30 min. No significant difference in potency is observed with these methods. Out of these methods, 56° C. for 10 min in presence of formaldehyde is selected because pertussis cell mass produced using this method is more homogeneous as compared to other methods mentioned above.

Process of Manufacturing Inactivated wP Antigen Comprises the Following Steps:

a). inactivation at 56° C. for 10-15 minutes in presence of formaldehyde of *Bordetella pertussis* strains 134 b). inactivation at 56° C. for 10-15 minutes in presence of formaldehyde of *Bordetella pertussis* strains 509 c). inactivation at 56° C. for 10-15 minutes in presence of formaldehyde of *Bordetella pertussis* strains 25525 and 6229 c). inactivation at 56° C. for 10-15 minutes in presence of formaldehyde of *Bordetella pertussis* strains 6229 d). subsequently mixing inactivated *Bordetella pertussis* strains 134, 509, 25525 and 6229 in a ratio of 1:1:0.25: 0.25.

e). optionally adsorbed onto aluminium based adjuvant.

The process is devoid of thiomersal and inactivated whole cell pertussis antigen remains non-clumpy and homogeneous thereby leading to reduced reactogenicity and giving better potency for a longer duration.

Example 10: Hexavalent Combination Vaccine Compositions Comprising Dose Reduced IPV, D, T, HepB, wP, and Hib Antigen are as Given Below

TABLE 29

Combination Vaccine comprising IPV (Salk Strain type 1(Mahoney) or type 2(MEF) or type 3(Saukett))

| S. No. | Formulation Components | Combination composition in accordance with the present disclosure [per 0.5 ml Dose] | | | | | | |
|---|---|---|---|---|---|---|---|---|
| | | 1 | 2 | 3 | 4 | 5 | 6 | 7 |
| 1 | Diphtheria Toxoid (D) | 22.5 Lf | 22.5 Lf | 22.5 Lf | 22.5 Lf | 22.5 Lf | 22.5 Lf | 22.5 Lf |
| 2 | Tetanus toxoid (T) | 7.5 Lf | 7.5 Lf | 7.5 Lf | 7.5 Lf | 7.5 Lf | 7.5 Lf | 7.5 Lf |
| 3 | Inactivated B. pertussis antigen (wP) | 15 IOU | 15 IOU | 15 IOU | 15 IOU | 15 IOU | 15 IOU | 15 IOU |
| 4 | HBs antigen | 12.5 µg | 12.5 µg | 12.5 µg | 12.5 µg | 12.5 µg | 12.5 µg | 12.5 µg |
| 5 | Hib PRP-TT conjugate antigen | 10 µg of PRP | 10 µg of PRP | 10 µg of PRP | 10 µg of PRP | 10 µg of PRP | 10 µg of PRP | 10 µg of PRP |
| 6 | Inactivated Polio Virus (IPV) | | | | | | | |
| | Type 1 (D antigen units) | 7.5 | 8 | 5 | 10 | 10 | 10 | 10 |
| | Type 2 (D antigen units) | 16 | 2 | 2 | 2 | 2 | 2 | 2 |
| | Type 3 (D antigen units) | 10 | 5 | 5 | 10 | 5 | 12 | 16 |
| 7 | Total Aluminium Content ($Al^{3+}$) | Not more than 0.9 mg | Not more than 0.9 mg | Not more than 0.9 mg | Not more than 0.9 mg | Not more than 0.9 mg | Not more than 0.9 mg | Not more than 0.9 mg |
| 8 | L-Histidine | 1.55 mg | 1.55 mg | 1.55 mg | 1.55 mg | 1.55 mg | 1.55 mg | 1.55 mg |
| 8 | 2-Phenoxyethanol | 3.25 mg | 3.25 mg | 3.25 mg | 3.25 mg | 3.25 mg | 3.25 mg | 3.25 mg |

Additionally adjusting the pH of the composition as disclosed above to about 6.0 to 7.0 with Sodium Hydroxide/Sodium Carbonate and make up the volume by adding normal saline (0.9%).

The composition may be devoid of IPV Type 2

May additionally comprise of one of the preservative combination iv. 2-Phenoxyethanol in an amount of 1 to 6 mg per 0.5 ml (v/v) and methylparaben in an amount of 0.1-1.5 mg per 0.5 ml (w/v); or v. 2-Phenoxyethanol in an amount of 1 to 6 mg per 0.5 ml (v/v) and propylparaben in an amount of 0.05-0.2 mg per 0.5 ml (w/v); or vi. 2-Phenoxyethanol in an amount of 1 to 6 mg per 0.5 ml (v/v), methylparaben in an amount of 0.1-1.5 mg per 0.5 ml (w/v) and propylparaben in an amount of 0.05-0.2 mg per 0.5 ml (w/v).

The Hexavalent Combination Vaccine Compositions comprising Dose reduced IPV, D, T, HepB, acellular pertussis, and Hib antigen may comprise of acellular pertussis antigen selected from—*Bordetella* toxin in detoxified form (in particular either genetically or chemically detoxified), in particular Pertussis toxoid; Filamentous Haemagglutinin; Pertactin; or Fimbriae. Particularly Pertussis toxoid: 1 to 50 micrograms (More particularly 8 µg); —Filamentous Haemagglutinin: 1 to 50 micrograms (More particularly 8 µg); —Pertactin: 1 to 20 micrograms (More particularly 2.5 µg); —Optionally, Fimbriae: 2 to 25 micrograms; per 0.5 ml.

TABLE 30

Combination Vaccine comprising IPV (Sabin Strain type 1 or type 2 or type 3)

| S. No. | Formulation Components | Combination composition in accordance with the present disclosure [per 0.5 ml Dose] | | |
|---|---|---|---|---|
| | | 1 | 2 | 3 |
| 1 | Diphtheria Toxoid (D) | 22.5 Lf | 22.5 Lf | 22.5 Lf |
| 2 | Tetanus toxoid (T) | 7.5 Lf | 7.5 Lf | 7.5 Lf |
| 3 | Inactivated B. pertussis antigen (wP) | 15 IOU | 15 IOU | 15 IOU |
| 4 | HBs antigen | 12.5 µg | 12.5 µg | 12.5 µg |
| 5 | Hib PRP-TT conjugate antigen | 10 µg of PRP | 10 µg of PRP | 10 µg of PRP |
| 6 | Inactivated Polio Virus (IPV) | | | |
| | Type 1 (D antigen units) | 5 | 2.5 | 7.5 |
| | Type 2 (D antigen units) | 16 | 8 | 16 |
| | Type 3 (D antigen units) | 10 | 5 | 10 |
| 7 | Total Aluminium Content ($Al^{3+}$) | Not more than 0.9 mg | Not more than 0.9 mg | Not more than 0.9 mg |
| 8 | L-Histidine | 1.55 mg | 1.55 mg | 1.55 mg |
| 8 | 2-Phenoxyethanol | 3.25 mg | 3.25 mg | 3.25 mg |

Additionally adjusting the pH of the composition as disclosed above to about 6.0 to 7.0 with Sodium Hydroxide/Sodium Carbonate and make up the volume by adding normal saline (0.9%).

The composition may be devoid of IPV Type 2

May additionally comprise of one of the preservative combination
  i. 2-Phenoxyethanol in an amount of 1 to 6 mg per 0.5 ml (v/v) and methylparaben in an amount of 0.1-1.5 mg per 0.5 ml (w/v); or
  ii. 2-Phenoxyethanol in an amount of 1 to 6 mg per 0.5 ml (v/v) and propylparaben in an amount of 0.05-0.2 mg per 0.5 ml (w/v); or
  iii. 2-Phenoxyethanol in an amount of 1 to 6 mg per 0.5 ml (v/v), methylparaben in an amount of 0.1-1.5 mg per 0.5 ml (w/v) and propylparaben in an amount of 0.05-0.2 mg per 0.5 ml (w/v).

The Hexavalent Combination Vaccine Compositions comprising Dose reduced IPV, D, T, HepB, acellular pertussis, and Hib antigen may comprise of acellular pertussis antigen selected from—*Bordetella* toxin in detoxified form (in particular either genetically or chemically detoxified), in particular Pertussis toxoid; Filamentous Haemagglutinin; Pertactin; or Fimbriae. Particularly Pertussis toxoid: 1 to 50 micrograms (More particularly 8 μg); —Filamentous Haemagglutinin: 1 to 50 micrograms (More particularly 8 μg); —Pertactin: 1 to 20 micrograms (More particularly 2.5 μg); —Optionally, Fimbriae: 2 to 25 micrograms; per 0.5 ml.

Example 11: Process for Preparation of Hexavalent Combination Vaccine Compositions Comprising Dose Reduced IPV, HBs, D, T, wP, and Hib PRP—Protein Conjugate is as Given Below a) adsorbing IPV (Sabin/Salk strain) bulk individually on Aluminium hydroxide, followed by pH adjustment to 6.2-6.6, more preferably 6.5.
b) adsorbing D on Aluminium phosphate, followed by pH adjustment to 5.5-6.5
c) adsorbing T on Aluminium phosphate, followed by pH adjustment to 5.5-6.5
d) adsorbing HBsAg on Aluminium phosphate, followed by pH adjustment to 6.0-6.5.
e) blending the mixture as obtained in step (b), (c), (d) by agitation at room temperature for 18-24 hours.
f) Blending the mixtures as obtained in step (a) and (e), followed by pH adjustment to 6.4-6.6 and agitation at room temperature for 60 minutes.
g) adding inactivated wP antigen/acellular pertussis antigen and a stabilizer (Histidine amino acid buffer solution 200 mM) to the above mixture in step (f), followed by agitation for 60 minutes and left in static condition for overnight at 2-8° C.
h) adding Hib antigen to the mixture obtained in step (g) at 2-8° C., followed by pH adjustment to 6.4-6.6.
i) Adjusting pH to 6.0 to 7.0 with Sodium Hydroxide/Sodium Carbonate and adding normal saline (0.9% NaCl) or WFI (q.s.) to make up the volume of the mixture obtained in step h, followed by agitation for 2 hours.
j) The process further comprises adding preservative to the mixture obtained in step (h) selected from:
  v. 2-Phenoxyethanol in an amount of 1 to 6 mg per 0.5 ml (v/v) and methylparaben in an amount of 0.1-1.5 mg per 0.5 ml (w/v); or
  vi. 2-Phenoxyethanol in an amount of 1 to 6 mg per 0.5 ml (v/v) and propylparaben in an amount of 0.05-0.2 mg per 0.5 ml (w/v); or
  vii. 2-Phenoxyethanol in an amount of 1 to 6 mg per 0.5 ml (v/v), methylparaben in an amount of 0.1-1.5 mg per 0.5 ml (w/v) and propylparaben in an amount of 0.05-0.2 mg per 0.5 ml (w/v);
  viii. 2-phenoxyethanol in an amount of 1 to 6 mg (v/v) per 0.5 ml as preservative.

Example 12: Adsorption and Potency Profile of Individual Antigens

TABLE 31

This table gives a brief on the percentage adsorption of individual antigens, and Potency profile of individual antigens in SIIPL Combination vaccine

| Test | Range | 0 Day |
|---|---|---|
| Dose | | 0.5 ml |
| Hepatitis B In-Vivo Potency R.P (95% CL) | (0.77-1.72) | 1.14 |
| Hib PRP Content (μg/0.5 ml) (Total PRP) | Actual value. | 11.32 μg/0.5 ml |
| Free PRP (%) | Actual value. | 1.7 |
| Diphtheria component potency (Lf/ml) | Actual value. | 42 |
| Tetanus component potency (Lf/ml) | Actual value. | 16.7 |
| Pertussis component potency (IU/dose) | NLT 4 IU/dose | 6.16 (3.34-11.41) |
| Adsorption Hepatitis-B (%) | Actual value. | 99.71 |
| Adsorption: Tetanus Component (%) | Actual value. | 100% |
| Adsorption: Diphtheria Component (%) | Actual value. | 105% |
| IPV Salk Strain D Antigen unit (DU/0.5 ml) ELISA | Type 1 = 10 DU/0.5 ml Type 2 = 2 DU/0.5 ml Type 3 = 10 DU/0.5 ml | 5.98 1.6 7.87 |
| IPV Salk Strain Invivo Efficacy | Type 1 (LL-UL) Type 3 (LL-UL) | 88.9% (25.4-266.9) 93.9% (38.7-245.0) |

TABLE 32

This table gives a brief on the percentage adsorption of individual antigens, and Potency profile of individual antigens in SIIPL Combination vaccine

| Test | Range | 0 Day |
|---|---|---|
| Dose | | 0.5 ml |
| Hepatitis B In-Vivo Potency R.P (95% CL) | (0.77-1.72) | 1.21 |
| Hib PRP Content (μg/0.5 ml) (Total PRP) | Actual value. | 11.87 μg/0.5 ml |
| Free PRP (%) | Actual value. | Not detectable |
| Diphtheria component potency (Lf/ml) | Actual value. | 42 |
| Tetanus component potency (Lf/ml) | Actual value. | 16.8 |
| Pertussis component potency (IU/dose) | NLT 4 IU/dose | 7.13 (3.45-15.85) |
| Adsorption Hepatitis-B (%) | Actual value. | 99.8 |
| Adsorption: Tetanus Component (%) | Actual value. | 100% |
| Adsorption: Diphtheria Component (%) | Actual value. | 105% |

TABLE 32-continued

This table gives a brief on the percentage adsorption of individual antigens, and Potency profile of individual antigens in SIIPL Combination vaccine

| Test | Range | 0 Day |
|---|---|---|
| IPV Sabin Strain | Type 1 = 5 DU/0.5 ml | 3.84 |
| D Antigen unit | Type 2 = 16 DU/0.5 ml | 8.66 |
| (DU/0.5 ml) ELISA | Type 3 = 10 DU/0.5 ml | 14.58 |
| IPV Sabin Strain | Type 1 | >100.0% |
| Invivo Efficacy | Type 2 | >100.0% |
|  | Type 3 | >100.0% |

What is claimed is:

1. A dose reduced Inactivated Polio vaccine (IPV) composition comprising:

diphtheria toxoid (D);

tetanus toxoid (T);

whole cell pertussis (wP);

hepatitis B virus surface antigen (HBsAg);

*Haemophilus influenzae* b PRP-Carrier protein conjugate (Hib); and an inactivated polio virus antigen selected from the group consisting of IPV Type 1 at a dose between 5 D-antigen units and 10 D-antigen units (DU), IPV Type 2 at a dose between 1 D-antigen units and 16 D-antigen units (DU), and IPV Type 3 at a dose between 1 D-antigen units and 16 D-antigen units (DU), wherein the IPV Type 1, IPV Type 2 or IPV Type 3 antigen is produced by formaldehyde inactivation in a non-phosphate buffer selected from the group consisting of TRIS, TBS, MOPS, HEPES and bicarbonate, and wherein the inactivated polio virus antigen is per 0.5 ml and the IPV Type 1, 2 and 3 antigens are adsorbed onto aluminum salt of hydroxide ($Al(OH)_3$) having a percentage adsorption of at least 90% and total aluminum content ($Al^{3+}$) in the composition is in an amount of 0.1 to 1.2 mg per 0.5 ml.

2. The composition as claimed in claim 1, wherein the IPV Type 1 antigen is the Mahoney strain (Salk Type 1) or Sabin strain; and/or wherein the IPV Type 2 antigen is the MEF-1 strain (Salk Type 2) or Sabin strain; and/or wherein the IPV Type 3 antigen is the Saukett strain (Salk Type 3) or Sabin strain.

3. The composition as claimed in claim 1, wherein 0.5 ml of the composition comprises:

the diphtheria toxoid (D) in an amount of 10 Lf to 25 Lf, adsorbed onto aluminum phosphate adjuvant having percentage adsorption of at least 50%;

a tetanus toxoid (T) in an amount of 2 Lf to 10 Lf, adsorbed onto aluminum phosphate adjuvant;

an inactivated whole cell pertussis (wP) in an amount of 12 IOU to 16 IOU;

a hepatitis B virus surface antigen (HBsAg) in an amount of 7 μg to 15 μg, adsorbed onto aluminum phosphate adjuvant;

a *Haemophilus influenzae* type b antigen (Hib) in an amount of 1 to 20 μg;

the IPV Type 1 antigen in an amount of 5-10 DU, the IPV Type 2 antigen in an amount of 1-16 DU, and the IPV Type 3 antigen in an amount of 1-16 DU; and L-Histidine in an amount of 0.5-5 mg.

4. The composition as claimed in claim 1, wherein the inactivated polio virus antigen dose is selected from the group consisting of:

i) IPV Type 1 (Sabin strain) in an amount of 2.5 DU, IPV Type 2 (Sabin strain) in an amount of 8 DU, and IPV Type 3 (Sabin strain) in an amount of 5 DU, per 0.5 ml;

ii) IPV Type 1 (Sabin strain) in an amount of 5 DU, IPV Type 2 (Sabin strain) in an amount of 16 DU, and IPV Type 3 (Sabin strain) in an amount of 10 DU, per 0.5 ml, iii) IPV Type 1 (Sabin strain) in an amount of 5 DU, IPV Type 2 (Sabin strain) in an amount of 8 DU, and IPV Type 3 (Sabin strain) in an amount of 10 DU, per 0.5 ml;

iv) IPV Type 1 (Mahoney strain) in an amount of 7.5 DU, IPV Type 2 (MEF-1 strain) in an amount of 16 DU, and IPV Type 3 (Saukett strain) in an amount of 10 DU, per 0.5 ml;

v) IPV Type 1 (Mahoney strain) in an amount of 8 DU, IPV Type 2 (MEF-1 strain) in an amount of 2 DU, and IPV Type 3 (Saukett strain) in an amount of 5 DU, per 0.5 ml;

vi) IPV Type 1 (Mahoney strain) in an amount of 10 DU, IPV Type 2 (MEF-1 strain) in an amount of 2 DU, and Type 3 (Saukett strain) in an amount of 5 DU, per 0.5 ml;

vii) IPV Type 1 (Mahoney strain) in an amount of 10 DU, IPV Type 2 (MEF-1 strain) in an amount of 2 DU, and IPV Type 3 (Saukett strain) in an amount of 10 DU, per 0.5 ml;

viii) IPV Type 1 (Mahoney strain) in an amount of 10 DU, IPV Type 2 (MEF-1 strain) in an amount of 2 DU, and IPV Type 3 (Saukett strain) in an amount of 12 DU, per 0.5 ml;

ix) IPV Type 1 (Mahoney strain) in an amount of 10 DU, IPV Type 2 (IMEF-1 strain) in an amount of 2 DU, and IPV Type 3 (Saukett strain) in an amount of 16 DU, per 0.5 ml;

x) IPV Type 1 (Mahoney strain) in an amount of 7.5 DU, IPV Type 2 (MEF-I strain) in an amount of 16 DU, and IPV Type 3 (Saukett strain) in an amount of 10 DU, per 0.5 ml; and xi) IPV Type 1 (Mahoney strain) in an amount of 5 DU, IPV Type 2 (MEF-1 strain) in an amount of 2 DU, and IPV Type 3 (Saukett strain) in an amount of 5 DU, per 0.5 ml.

5. The composition as claimed in claim 1, wherein the composition is a single dose free of preservatives.

6. The composition as claimed in claim 1, wherein the composition is a multi-dose composition comprising one or more preservatives.

7. The composition as claimed in claim 6, wherein the one or more preservatives comprise:

i. 2-Phenoxyethanol in an amount of 2.5 mg and methylparaben in an amount of 0.9 mg per 0.5 ml;

ii. 2-Phenoxyethanol in an amount of 2.5 mg and propylparaben in an amount of 0.1 mg per 0.5 ml; or iii. 2-Phenoxyethanol in an amount of 2.5 mg, methylparaben in an amount of 0.9 mg and propylparaben in an amount of 0.1 mg per 0.5 ml.

8. The composition as claimed in claim 1, wherein the composition comprises a buffer selected from the group consisting of carbonate, phosphate, acetate, succinate, borate, citrate, lactate, gluconate, tartrate, MEM, TRIS, HEPES, piperazine-N, N'-bis (PIPES), 2-ethanesulfonic acid (MES) and sodium chloride in a concentration of 0.5% to 1.5%.

9. The composition as claimed in claim 1, wherein the 0.5 ml of the composition comprises: the D antigen in an amount of 22.5 Lf; the T antigen in an amount of 7.5 Lf; the wP antigen in an amount of 15 IOU; the HBsAg in an amount of 12.5 µg; the Hib antigen in an amount of 10 µg; IPV Type 1 antigen (Mahoney strain) in an amount of 5, 7.5, 8 or 10 DU, IPV Type 2 antigen (MEF-1 strain) in an amount of 2 or 16 DU, and IPV Type 3 antigen (Saukett strain) in an amount of 5, 10, 12 or 16 DU; a total aluminum content (Al3+) not more than 0.9 mg; 2-Phenoxyethanol in an amount of 3.25 mg; and L-Histidine in an amount of 1.55 mg.

10. The composition as claimed in claim 9, wherein the IPV Type 1 antigen (Mahoney strain) is in an amount of 10 DU, the IPV Type 2 antigen (MEF-1 strain) is in an amount of 2 DU, and the IPV Type 3 antigen (Saukett strain) is in an amount of 10 DU.

11. The composition as claimed in claim 9, wherein the IPV Type 1 antigen (Mahoney strain) is in an amount of 10 DU and the IPV Type 3 antigen (Saukett strain) is in an amount of 10 DU.

12. The composition as claimed in claim 1, wherein the 0.5 ml of the composition comprises: the D antigen in an amount of 22.5 Lf; the T antigen in an amount of 7.5 Lf; the wP antigen in an amount of 15 IOU; the HBsAg in an amount of 12.5 µg; the Hib antigen in an amount of 10 µg; IPV Type 1 antigen (Sabin strain) in an amount of 2.5 or 5 or 7.5 DU, IPV Type 2 antigen (Sabin strain) in an amount of 8 or 16 DU, and IPV Type 3 antigen (Sabin strain) in an amount of 5 or 10 DU; a total aluminium aluminum content ($Al^{3+}$) not more than 0.9 mg; 2-Phenoxyethanol in an amount of 3.25 mg; and L-Histidine in an amount of 1.55 mg.

13. The composition as claimed in claim 12, wherein the IPV Type 1 antigen (Sabin strain) is in an amount of 5 DU, the IPV Type 2 antigen (Sabin strain) is in an amount of 16 DU, and the IPV Type 3 antigen (Sabin strain) is in an amount of 10 DU.

14. The composition as claimed in claim 12, wherein the IPV Type 1 antigen (Sabin strain) is in an amount of 5 DU and the IPV Type 3 antigen (Sabin strain) is in an amount of 10 DU.

15. A process of manufacturing a dose reduced Inactivated Polio vaccine (IPV) composition comprising:
(i) an inactivated polio virus antigen selected from the group consisting of IPV Type 1 at a dose less than 15 D-antigen units (DU), IPV Type 2 at a dose less than 18 D-antigen unit (DU), and IPV Type 3 at a dose less than 17 D-antigen unit (DU), per 0.5 ml;
(ii) a diphtheria toxoid (D) antigen in an amount of 1 to 50 Lf per 0.5 ml;
(iii) a tetanus toxoid (T) antigen in an amount of 1 to 30 Lf per 0.5 ml;
(iv) a whole cell pertussis (wP) antigen in an amount of 1 to 50 IOU per 0.5 ml or acellular pertussis (aP) comprising one or more of modified adenylate cyclase, Pertussis toxoid (PT) 1-50 µg, Filamentous hemagglutinin (FHA) 1-50 µg, Penactin (P69 or PRN) 1-20 µg or Fimbrial proteins (FIM 1, 2 and 3) 2-25 µg; per 0.5 ml;
(v) a hepatitis B virus surface antigen (HBsAg) in an amount of 1 to 20 µg per 0.5 ml; and
(vi) a *Haemophilus influenzae* type b antigen (Hib) in an amount of 1 to 20 µg per 0.5 ml;
wherein the IPV Type 1, IPV Type 2 or IPV Type 3 antigen is produced by formaldehyde inactivation in a non-phosphate buffer selected from the group consisting of TRIS, TBS, MOPS, HEPES and bicarbonate;

the process comprising the steps of:
a) adsorbing the IPV (Sabin/Salk strain) bulk individually on aluminium hydroxide, followed by pH adjustment to 6.2-6.6;
b) adsorbing the D on aluminium phosphate, followed by pH adjustment to 5.5-6.5;
c) adsorbing the T on aluminium phosphate, followed by pH adjustment to 5.5-6.5;
(d) adsorbing the HBsAg on aluminium phosphate, followed by pH adjustment to 6.0-6.5;
(e) blending a mixture obtained from steps b), c), and d) by agitation at room temperature for 18-24 hours;
(f) blending a content of step a) with the mixture obtained in step e), followed by pH adjustment to 6.4-6.6 and agitation at room temperature for 60 minutes;
(g) adding an inactivated wP antigen/acellular pertussis antigen and a stabilizer (Histidine amino acid buffer solution 100-300 mM) to the mixture in step f), followed by agitation for 60 minutes and left in static condition for overnight at 2-8° C.;
(h) adding the Hib antigen to the mixture obtained in step g) at 2-8° C., followed by pH adjustment to 6.4-6.6; and
(i) adjusting the pH to 6.0 to 7.0 with sodium hydroxide/sodium carbonate and adding normal saline (0.9% NaCl) or Water For Injection (WFI) (q.s.) to make up a volume of the mixture obtained in step h), followed by agitation for 2 hours.

16. The process as claimed in claim 15, wherein the process further comprises adding a preservative to the mixture obtained in step h) selected from the group consisting of:
i. 2-Phenoxyethanol in an amount of 1 to 6 mg per 0.5 ml and methylparaben in an amount of 0.1-1.5 mg per 0.5 ml;
ii. 2-Phenoxyethanol in an amount of 1 to 6 mg per 0.5 ml and propylparaben in an amount of 0.05-0.2 mg per 0.5 ml;
iii. 2-Phenoxyethanol in an amount of 1 to 6 mg per 0.5 ml, methylparaben in an amount of 0.1-1.5 mg per 0.5 ml and propylparaben in an amount of 0.05-0.2 mg per 0.5 ml; and
iv. 2-phenoxyethanol in an amount of 1 to 6 mg per 0.5 ml as preservative.

17. The process as claimed in claim 15, wherein
i) the diphtheria toxoid and the tetanus toxoid is purified using Gel Permeation chromatography and stabilized using an amino acid buffer solution (histidine 100-300 mM) have a monomeric content of at least 80%,
ii) the Hib antigen is in the form of a polyribosyl-ribitol-phosphate (PRP)-carrier protein conjugate prepared using a cyanylation conjugation process and subsequently blended at low temperature in presence of an excipient with greater stability with minimum free PRP release and improved immunogenicity, and
iii) the whole cell pertussis antigen is added at a later stage in a blend minimizing hydrolysis based degradation and providing a stable and immunogenic wP antigen.

18. A method for producing a composition comprising Enteroviral poliovirus particles, wherein the method comprises the steps of:
a) purifying the Enteroviral poliovirus particles in a medium comprising a phosphate buffer;
b) exchanging the phosphate buffer of the purified Enteroviral poliovirus particles of step a) for a non-ph buffer selected from the group consisting of TRIS, TBS, MOPS, HEPES or bicarbonate buffer and a combination thereof;

c) stabilizing the purified and buffer-exchanged Enteroviral poliovirus particles of step b);

d) inactivating the Enteroviral poliovirus particles of step c) by:

(i) adding formalin to the purified Enteroviral poliovirus particles in the non-phosphate buffer of step b) and stirring for 7 days;

(ii) filtering the product of step (i);

(iii) adding formalin to the product of step (ii) and stirring for 6 days; and (iv) filtering the product of step (iii), wherein the non-phosphate buffer is present at a concentration of 30-70 mM, aggregation of the Enteroviral poliovirus particles is prevented or reduced and the D-antigen losses are reduced post inactivation by 8 to 10 fold as compared to inactivation in phosphate buffer.

19. The method as claimed in claim 18, further comprising adsorbing the inactivated Enteroviral poliovirus particles on an aluminium salt adjuvant, wherein the percentage adsorption on the aluminium salt adjuvant is at least 90%.

20. A combination vaccine comprising a vaccine portion and a buffer portion, wherein the vaccine portion consists essentially of:

diphtheria toxoid (D);

tetanus toxoid (T);

whole cell pertussis (wP);

hepatitis B virus surface antigen (HBsAg);

*Haemophilus influenzae* b PRP-Carrier protein conjugate (Hib); and an inactivated polio virus antigen selected from the group consisting of IPV Type 1 at a dose between 5 D-antigen units and 10 D-antigen units (DU), IPV Type 2 at a dose between 1 D-antigen units and 16 D-antigen units (DU), and IPV Type 3 at a dose between 1 D-antigen units and 16 D-antigen units (DU)

wherein the IPV Type 1, IPV Type 2 or IPV Type 3 antigen is produced by formaldehyde inactivation in a non-phosphate buffer selected from the group consisting of TRIS, TBS, MOPS, HEPES and bicarbonate.

21. The combination vaccine of claim 20, wherein the buffer portion comprises a histidine buffer.

22. The combination vaccine of claim 21, wherein the histidine buffer comprises L-histidine.

* * * * *